United States Patent
Ceusters et al.

(10) Patent No.: US 9,314,991 B2
(45) Date of Patent: *Apr. 19, 2016

(54) ELASTIC LAMINATE

(75) Inventors: Robert Ceusters, Turnhout (BE); Johannes H. A. De Jong, Lichtaart (BE)

(73) Assignee: Avery Dennison Corporation, Glendale, CA (US)

(*) Notice: Subject to any disclaimer, the term of this patent is extended or adjusted under 35 U.S.C. 154(b) by 1853 days.

This patent is subject to a terminal disclaimer.

(21) Appl. No.: 12/439,190

(22) PCT Filed: Aug. 31, 2007

(86) PCT No.: PCT/US2007/077359
§ 371 (c)(1),
(2), (4) Date: May 22, 2009

(87) PCT Pub. No.: WO2008/028114
PCT Pub. Date: Mar. 6, 2008

(65) Prior Publication Data
US 2009/0254057 A1 Oct. 8, 2009

Related U.S. Application Data

(60) Provisional application No. 60/824,261, filed on Aug. 31, 2006, provisional application No. 60/862,252, filed on Oct. 20, 2006, provisional application No. 60/913,059, filed on Apr. 20, 2007, provisional (Continued)

(51) Int. Cl.
*B32B 3/10* (2006.01)
*A61F 13/49* (2006.01)
(Continued)

(52) U.S. Cl.
CPC .............. *B32B 3/10* (2013.01); *A61F 13/4902* (2013.01); *A61F 13/49012* (2013.01);
(Continued)

(58) Field of Classification Search
CPC ........... A61F 13/4902; A61F 13/49017; A61F 13/5622; A61F 13/49015; A61F 13/49012; B32B 3/10; B32B 27/12; Y10T 442/601; Y10T 156/1064; Y10T 428/24612; Y10T 428/24314
USPC .......... 428/105, 136, 138; 442/328, 381, 394; 156/229, 257, 263
See application file for complete search history.

(56) References Cited

U.S. PATENT DOCUMENTS

| 829,805 A | 8/1906 | Sackville |
| 2,473,404 A | 6/1949 | Young |

(Continued)

FOREIGN PATENT DOCUMENTS

| DE | 0 191 355 | 8/1986 |
| DE | 3710037 | 3/1987 |

(Continued)

OTHER PUBLICATIONS

International Search Report and Written Opinion issued in PCT/US2007/077359 dated Dec. 4, 2007.

(Continued)

*Primary Examiner* — Nathan Van Sell
(74) *Attorney, Agent, or Firm* — Avery Dennison Corporation

(57) ABSTRACT

A method of making an elastic laminate (10) comprising the steps of providing an intermediate elastic/fabric laminate (16) and segmenting the fabric layer (30) into fabric segments (31) by forming interruptions (32) which extend through the fabric thickness. The interruption-forming step comprising cutting/slitting/scoring the fabric layer (30) to form proximal/distal regions (33/34) of the interruptions (31) and incrementally rupturing the fabric layer (30) to form the remaining distal/proximal interruption region (34/33).

21 Claims, 39 Drawing Sheets

Related U.S. Application Data application No. 60/913,048, filed on Apr. 20, 2007, provisional application No. 60/912,983, filed on Apr. 20, 2007, provisional application No. 60/941,431, filed on Jun. 1, 2007, provisional application No. 60/941,402, filed on Jun. 1, 2007, provisional application No. 60/941,420, filed on Jun. 1, 2007.

(51) Int. Cl.
    *A61F 13/56*     (2006.01)
    *B32B 27/12*     (2006.01)

(52) U.S. Cl.
    CPC .... *A61F 13/49015* (2013.01); *A61F 13/49017* (2013.01); *A61F 13/5622* (2013.01); *B32B 27/12* (2013.01); *Y10T 156/1064* (2015.01); *Y10T 428/24314* (2015.01); *Y10T 428/24612* (2015.01); *Y10T 442/601* (2015.04)

(56) References Cited

U.S. PATENT DOCUMENTS

| | | |
|---|---|---|
| 2,618,012 A | 11/1952 | Milne |
| 2,626,422 A | 1/1953 | Lammertse |
| 2,841,820 A | 7/1958 | Pfeiffer |
| 3,078,504 A | 2/1963 | Koppehele |
| 3,193,873 A | 7/1965 | Wienand |
| 3,261,903 A | 7/1966 | Carr |
| 3,296,351 A | 1/1967 | Rasmussen |
| 3,577,586 A | 5/1971 | Kalwaites |
| 3,719,540 A | 3/1973 | Hall |
| 3,800,796 A | 4/1974 | Jacob |
| 3,833,973 A | 9/1974 | Schwarz |
| 3,949,127 A | 4/1976 | Ostermeier et al. |
| 4,063,559 A | 12/1977 | Tritsch |
| 4,116,892 A | 9/1978 | Schwarz |
| 4,389,212 A | 6/1983 | Tritsch |
| 4,643,729 A | 2/1987 | Laplanche |
| 4,731,066 A | 3/1988 | Korpman |
| 4,787,897 A | 11/1988 | Torimae et al. |
| 4,795,456 A | 1/1989 | Borgers et al. |
| 4,862,564 A | 9/1989 | Kwack |
| 4,968,313 A | 11/1990 | Sabee |
| 5,038,989 A | 8/1991 | Beliveau |
| 5,057,097 A | 10/1991 | Gesp |
| 5,072,493 A | 12/1991 | Hommes et al. |
| 5,143,679 A | 9/1992 | Weber et al. |
| 5,156,793 A | 10/1992 | Buell et al. |
| 5,167,897 A | 12/1992 | Weber et al. |
| 5,344,691 A | 9/1994 | Hanschen et al. |
| 5,468,428 A | 11/1995 | Hanschen et al. |
| 5,628,097 A | 5/1997 | Benson et al. |
| 5,729,878 A | 3/1998 | Kurihara et al. |
| 5,804,021 A * | 9/1998 | Abuto et al. .................. 156/252 |
| 5,916,661 A | 6/1999 | Benson et al. |
| 6,069,097 A | 5/2000 | Suzuki et al. |
| 6,461,715 B1 | 10/2002 | Guenther et al. |
| 6,551,436 B1 | 4/2003 | Flohr et al. |
| 6,632,504 B1 | 10/2003 | Gillespie et al. |
| 6,712,921 B2 | 3/2004 | Mitsuno et al. |
| 7,001,475 B2 | 2/2006 | Ausen et al. |
| 7,135,213 B2 | 11/2006 | Maki et al. |
| 2003/0105446 A1* | 6/2003 | Hutson et al. ............ 604/385.22 |
| 2003/0124291 A1 | 7/2003 | Ausen et al. |
| 2005/0025937 A1 | 2/2005 | Maki et al. |
| 2005/0215972 A1 | 9/2005 | Roe et al. |
| 2005/0249915 A1 | 11/2005 | Wood et al. |
| 2006/0148359 A1 | 7/2006 | Van Gompel et al. |
| 2007/0040000 A1 | 2/2007 | Jackson et al. |
| 2007/0040301 A1 | 2/2007 | Jackson |
| 2007/0105472 A1 | 5/2007 | Marche |

FOREIGN PATENT DOCUMENTS

| | | | |
|---|---|---|---|
| DE | 19522743 | 6/1995 | |
| DE | 196 47 459 | 5/1998 | |
| EP | 0 596 532 | 5/1994 | |
| EP | 0 936 061 | 12/1998 | |
| EP | 1 277 868 | 5/2002 | |
| WO | 96/10481 | 4/1996 | |
| WO | WO 2008060204 A1 * | 5/2008 | ............ B29C 55/02 |

OTHER PUBLICATIONS

International Search Report and Written Opinion issued in corresponding PCT/US2007/077349 dated Jun. 13, 2008.
International Preliminary Report on Patentability issued in corresponding PCT/US2007/077349 dated Mar. 12, 2009.
International Preliminary Report on Patentability issued in corresponding PCT/US2007/077359 dated Jan. 20, 2009.
International Search Report and Written Opinion issued in corresponding PCT/US2007/077367 dated Dec. 4, 2007.
International Preliminary Report on Patentability issued in corresponding PCT/US2007/077367 dated Mar. 12, 2009.

* cited by examiner

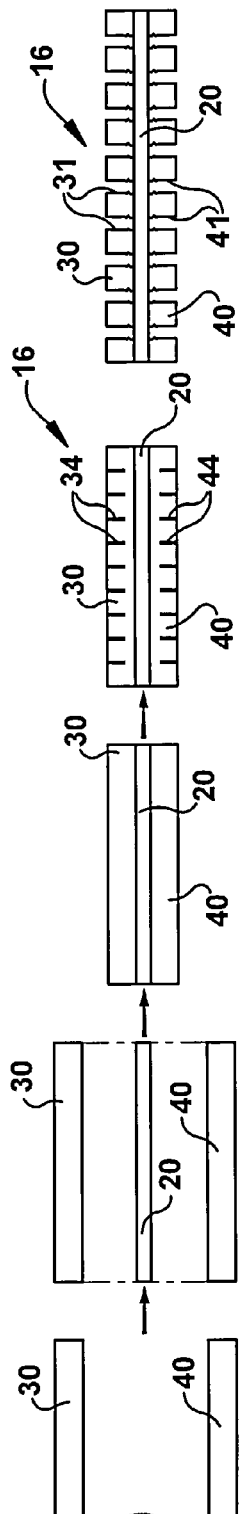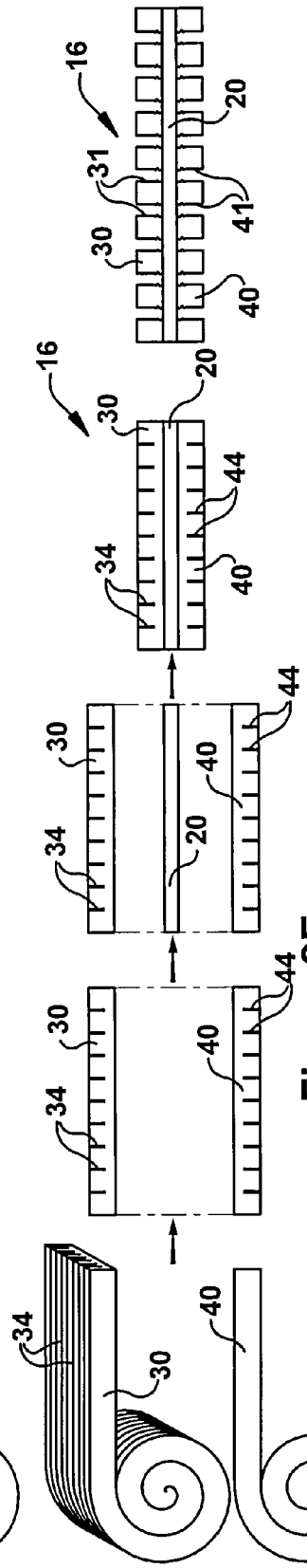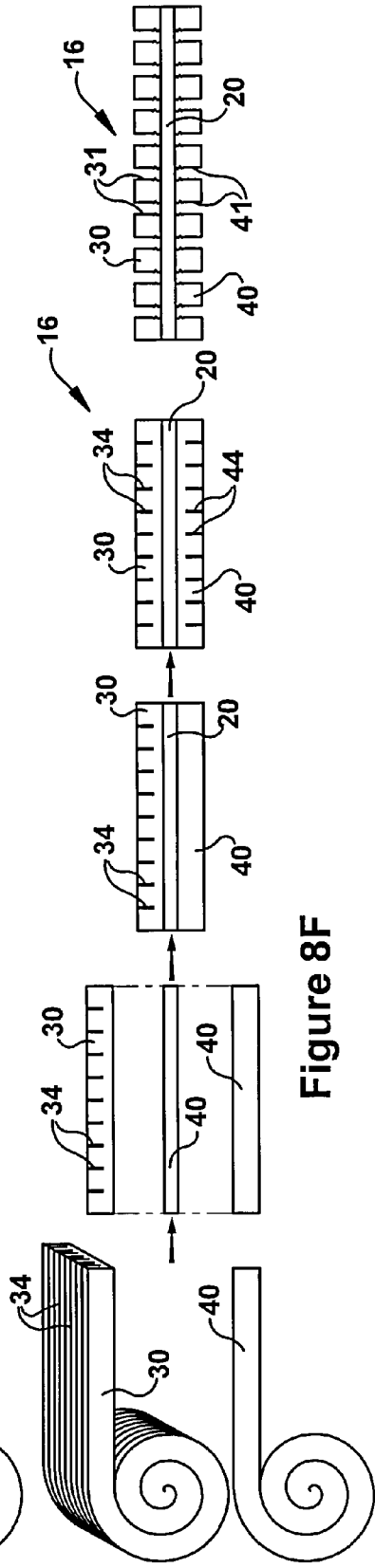

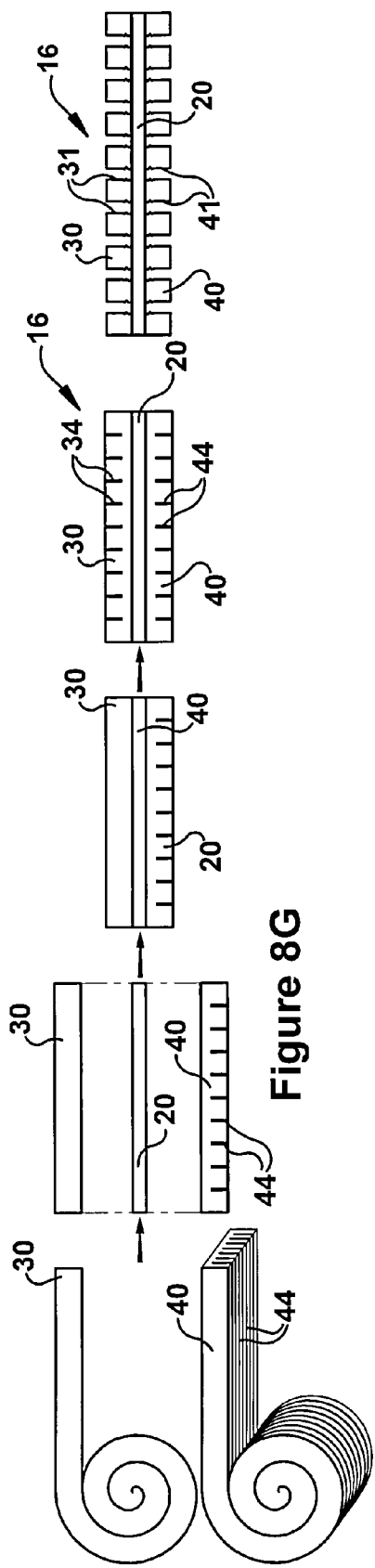
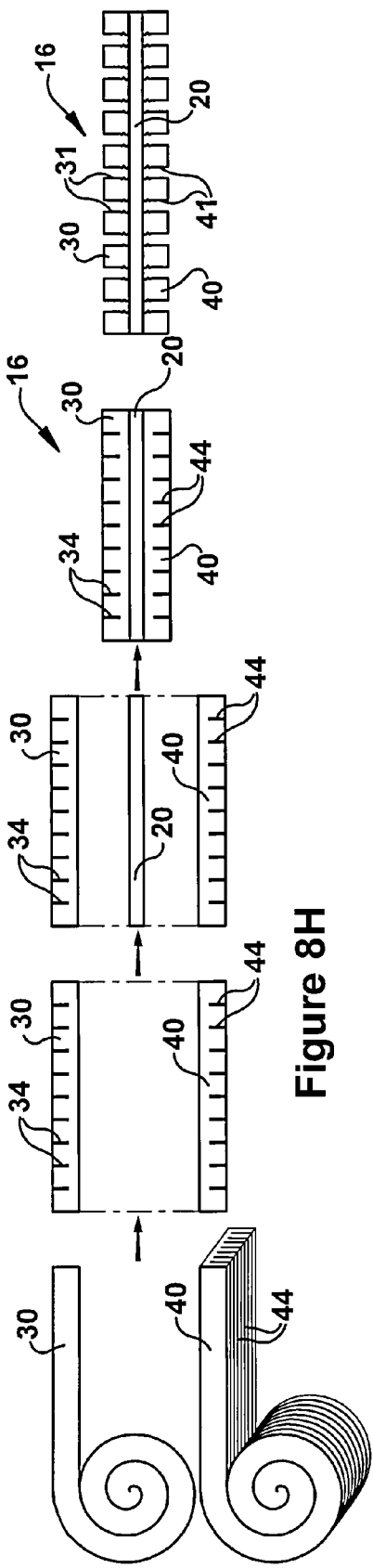
Figure 8G
Figure 8H

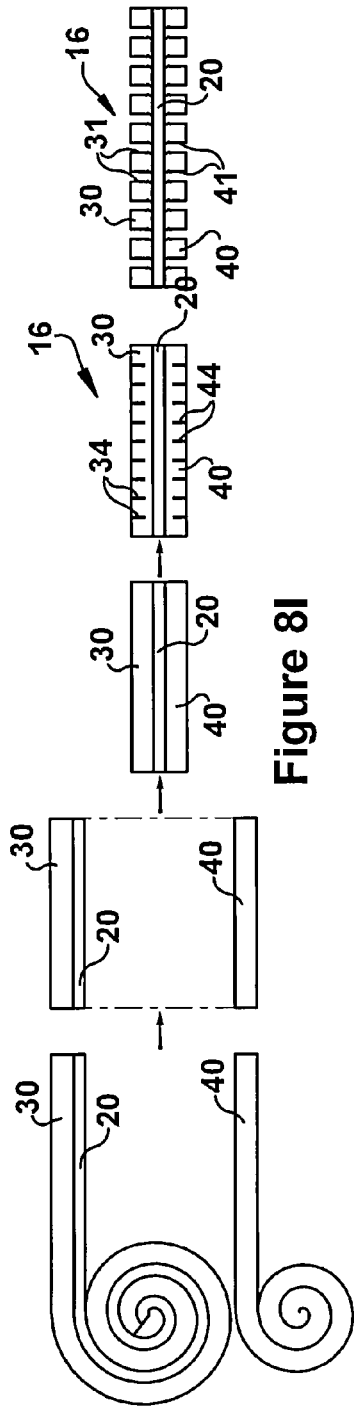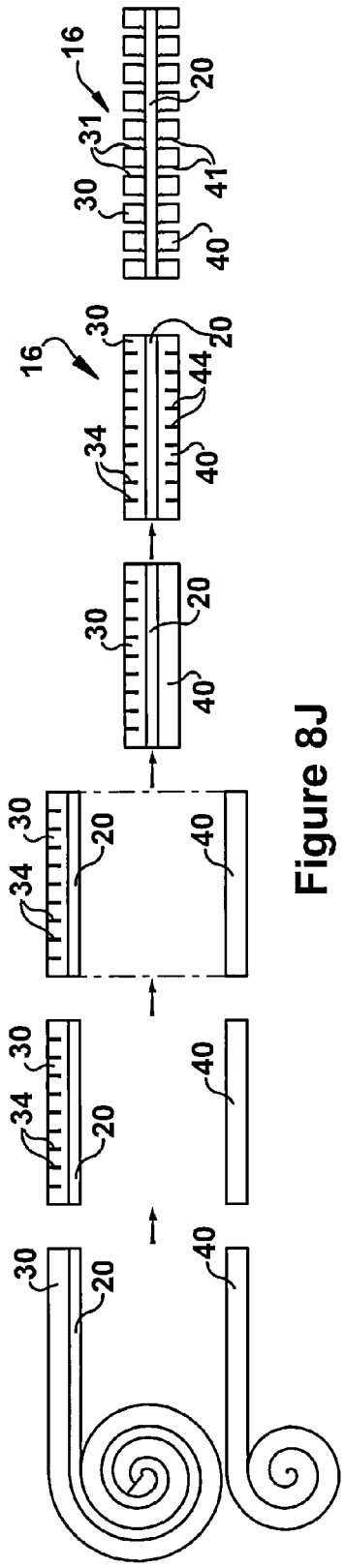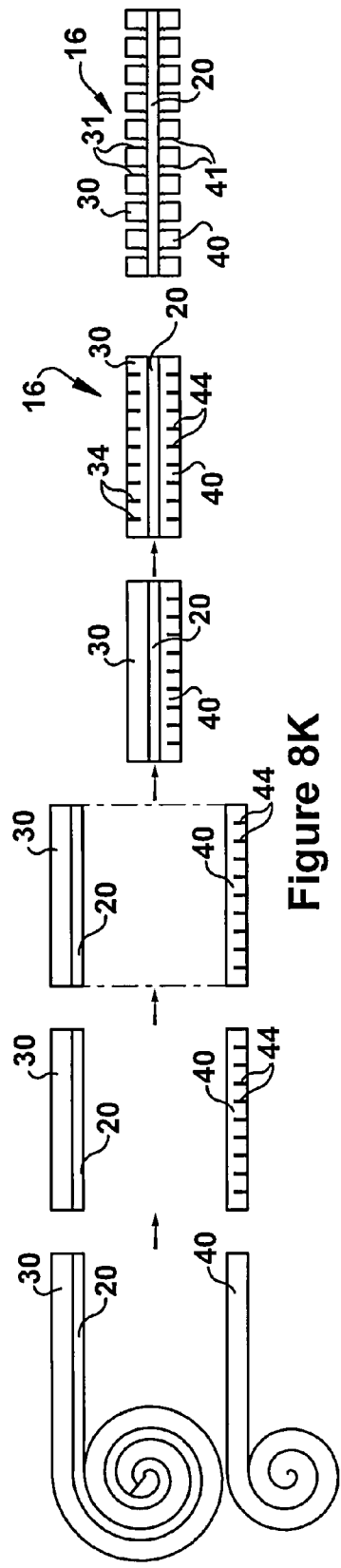

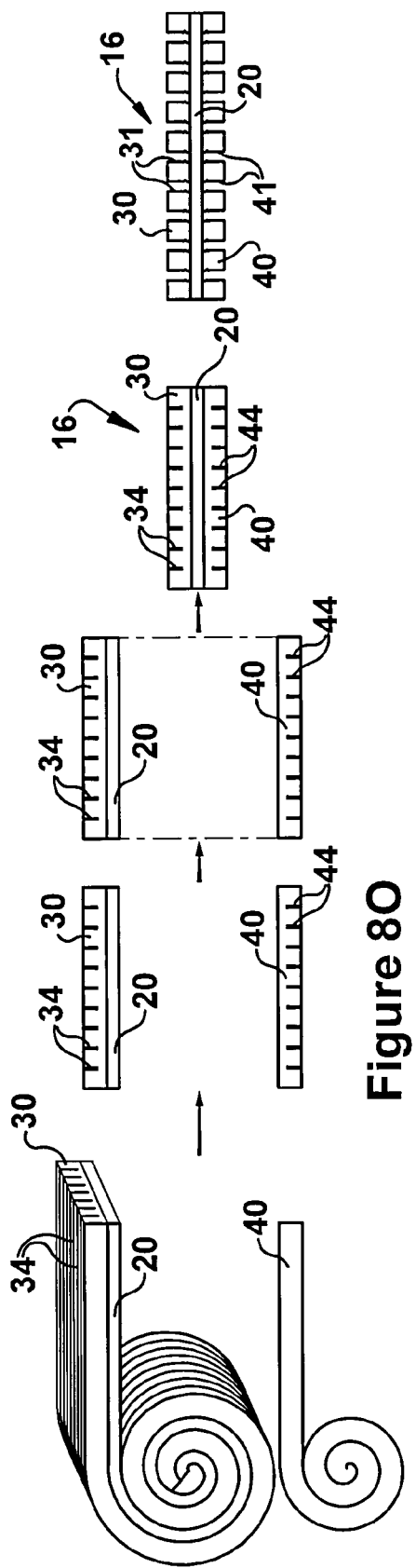
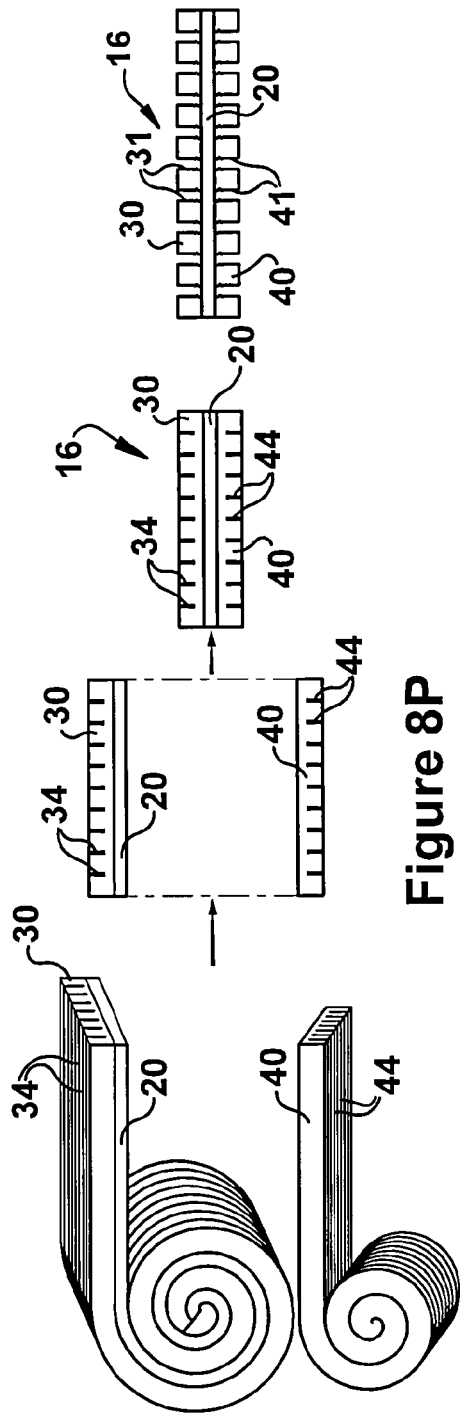
Figure 8O
Figure 8P

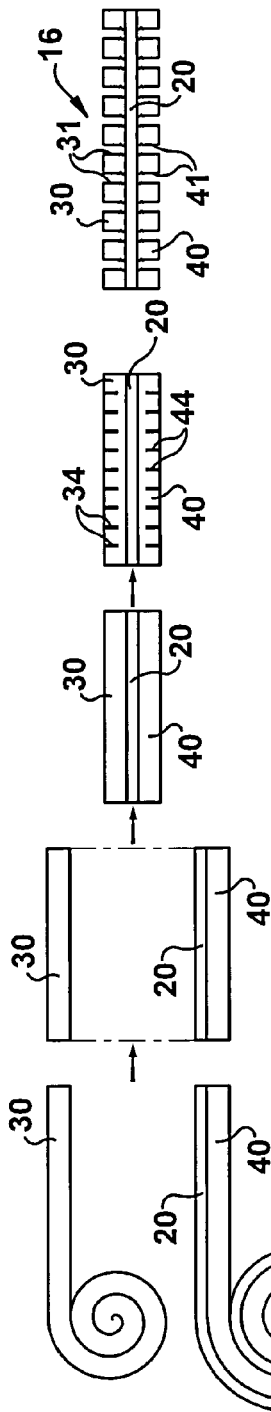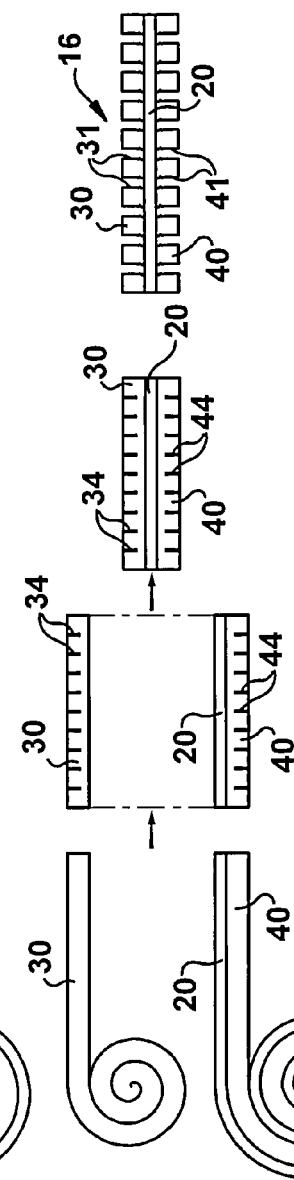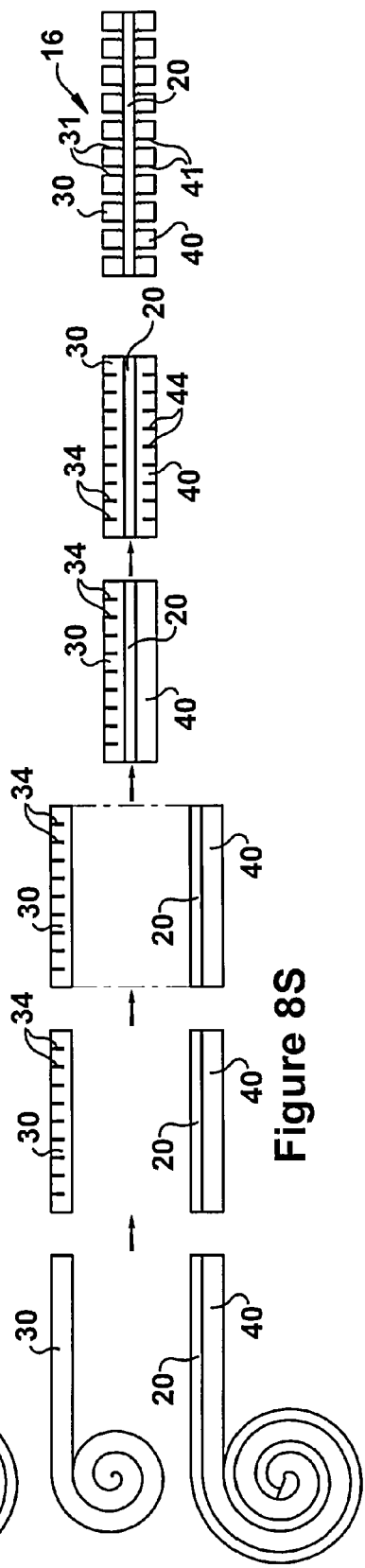

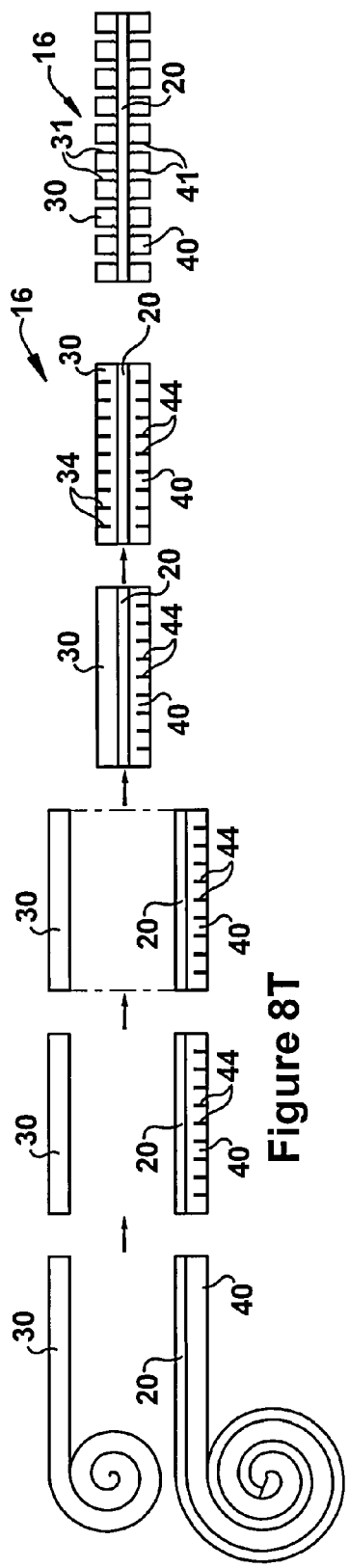
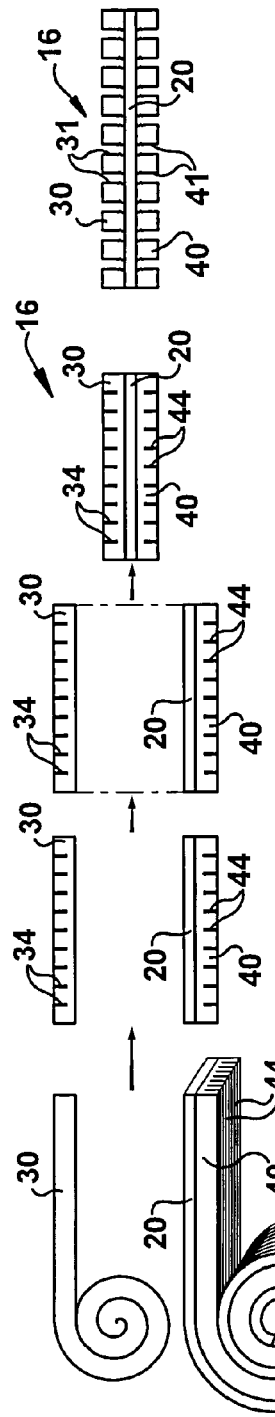
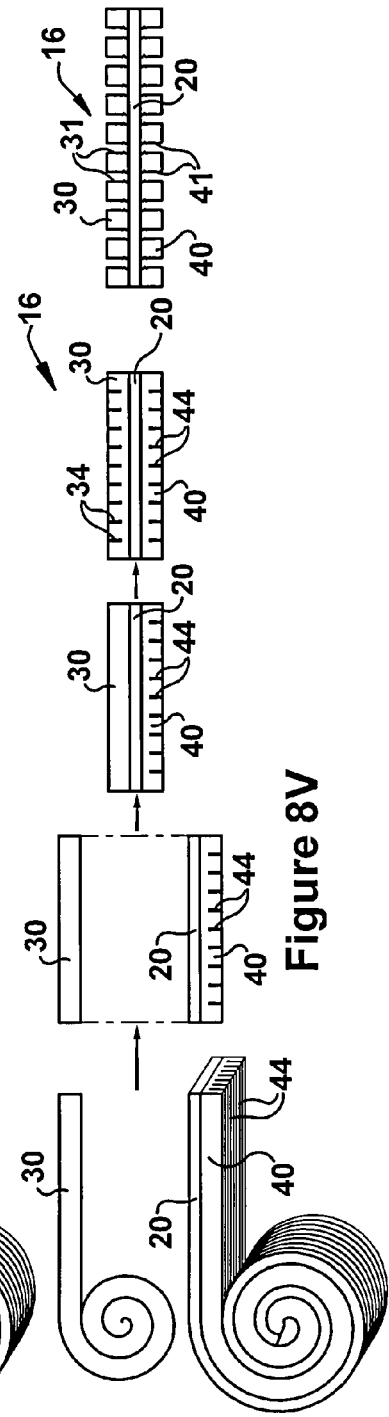
Figure 8T
Figure 8U
Figure 8V

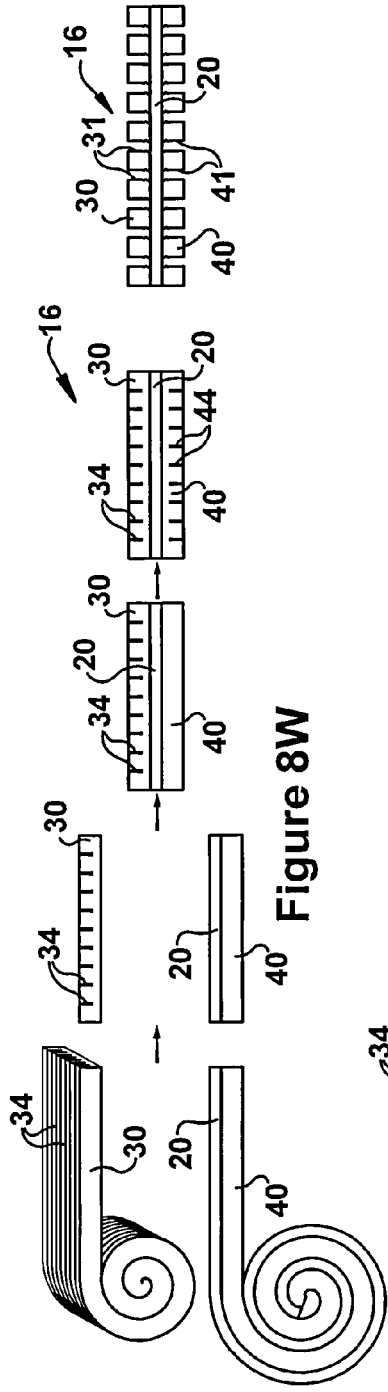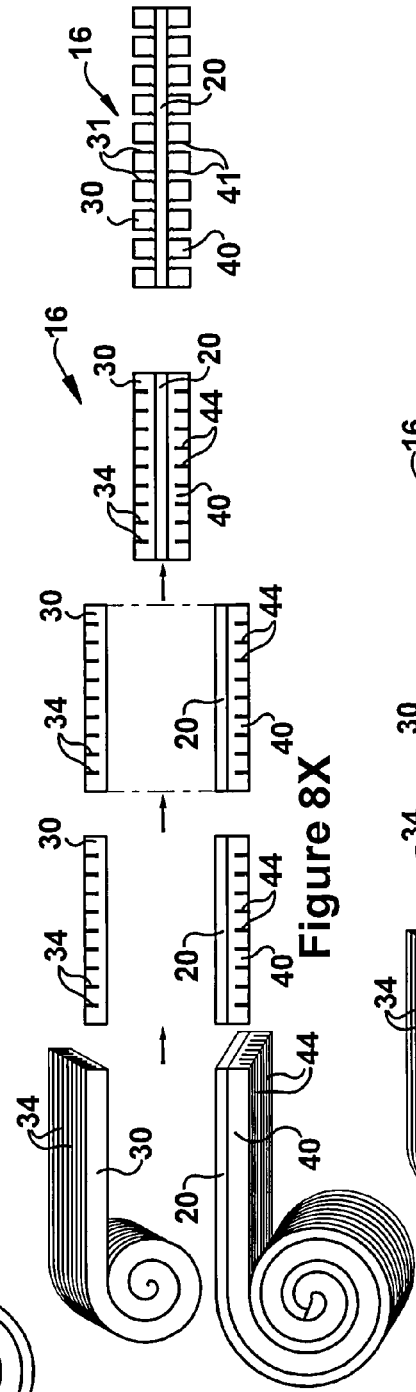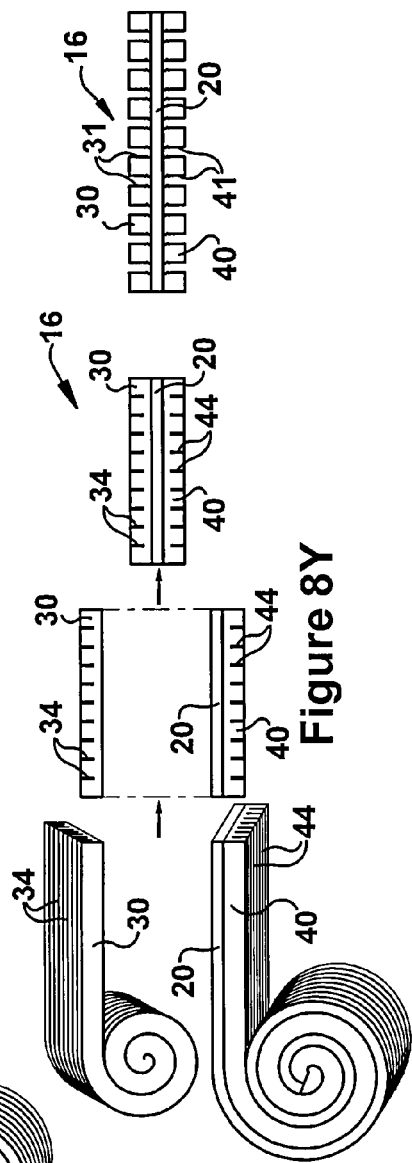

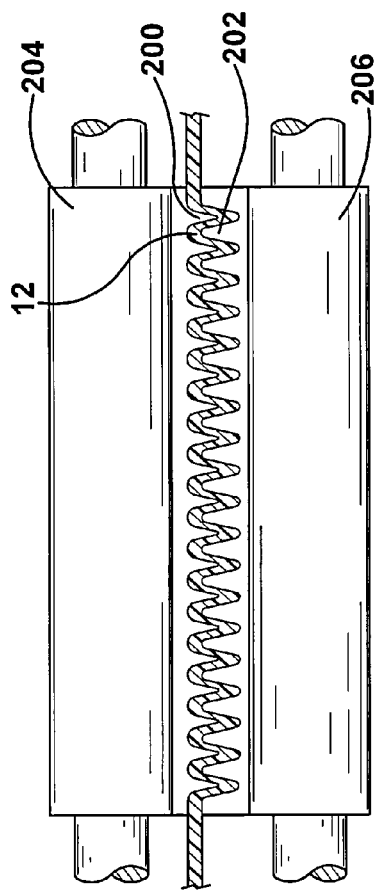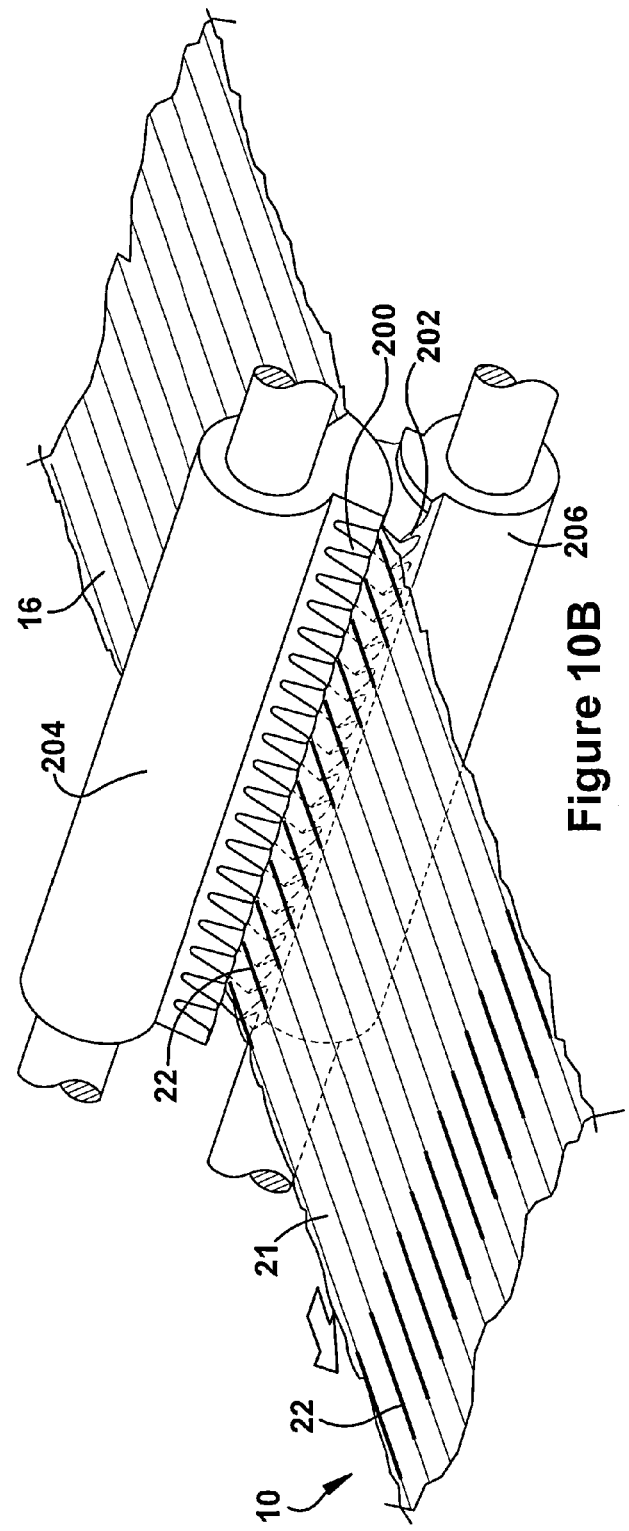
Figure 10A
Figure 10B

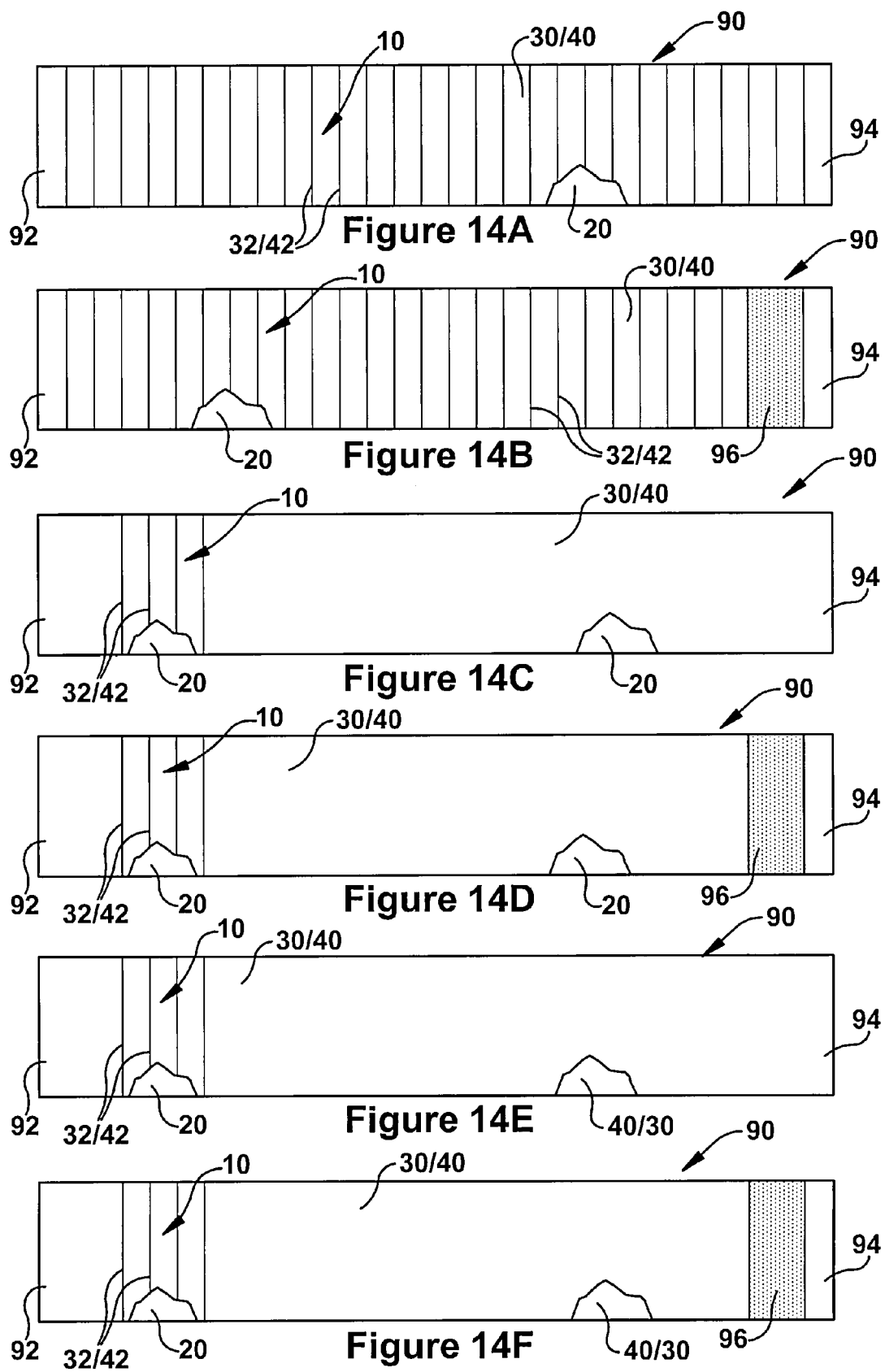

ELASTIC LAMINATE

The present application is a 371 of International Application No. PCT/US2007/077359, which was published in English on Mar. 6, 2008, and is incorporated herein by reference in its entirety.

An elastic laminate, comprising an elastic layer and one or more fabric layer(s), can be used in a variety of situations where elasticity is required or desired for one reason or another. For example, in the field of disposable absorbent articles (e.g., diapers, incontinence briefs, etc.), an elastic laminate can be used as, or incorporated into, a side panel for attachment to a rear chassis portion. Belts, performing a similar function, can also include an elastic laminate. A fastening tape, for attaching a rear chassis portion to a front chassis portion, can also comprise an elastic laminate. An elastic laminate can be used to form the diaper/brief chassis itself, or portions/regions thereof (e.g., waist regions in a front/rear chassis portion, leg-opening regions in a crotch chassis portion, etc.). With these and other applications, it is often necessary or desirable to use a fabric layer (e.g., a nonwoven fabric layer) as the next-to-the-skin layer and/or the exposed layer.

SUMMARY

An elastic laminate is provided which is an excellent candidate for incorporation into a diaper product and/or any other product requiring elastic properties. The elastic activation of the laminate comprises rupturing a fabric layer (e.g., a nonelastic nonwoven layer) whereby the fabric is separated into fabric segments which diverge/converge to allow laminate elongation/recovery. Because the fabric is not stretched, creased, or otherwise deformed during activation, it assumes a very flat neat appearance when the laminate is in the relaxed state. Moreover, because the fabric-rupturing is accomplished by applying a series of discrete rupture-inducing forces, the results are predictable and repeatable, while still welcoming a wide range of nonwoven fabrics for participation.

DRAWINGS

FIGS. 10A-10D, are plan, perspective and close-up views of a rupturing inducing device.

FIGS. 14A-14F are plan views of belts including a stretchable laminate.

DETAILED DESCRIPTION

Figure 1A:
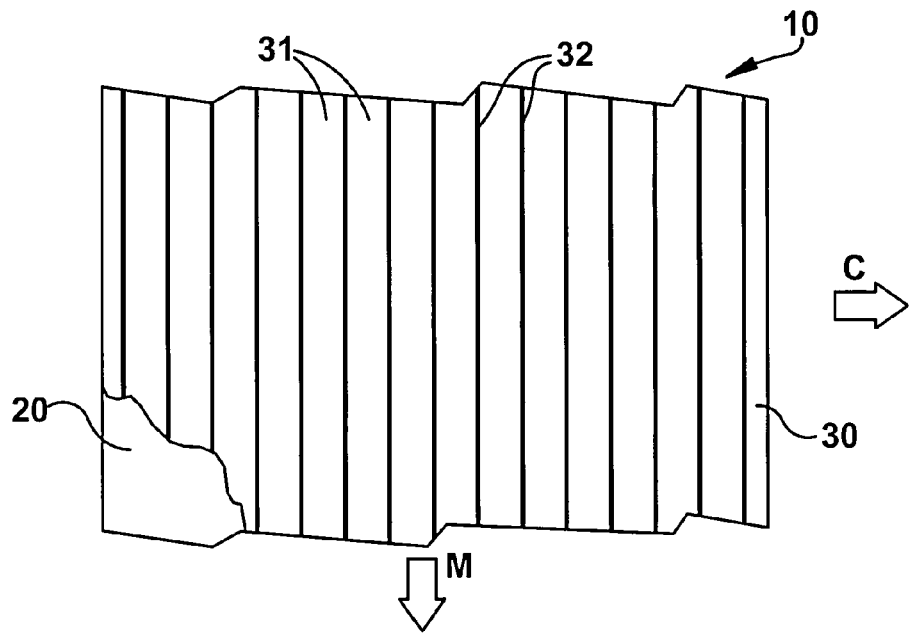
FIGS. 1A-1C are a plan view and side views of an elastic laminate comprising an elastic layer and fabric layer having a series of interruptions, the laminate being shown in a relaxed state in FIGS. 1A and 1B, and in an elongated state in FIG. 1C.
Figure 1B:
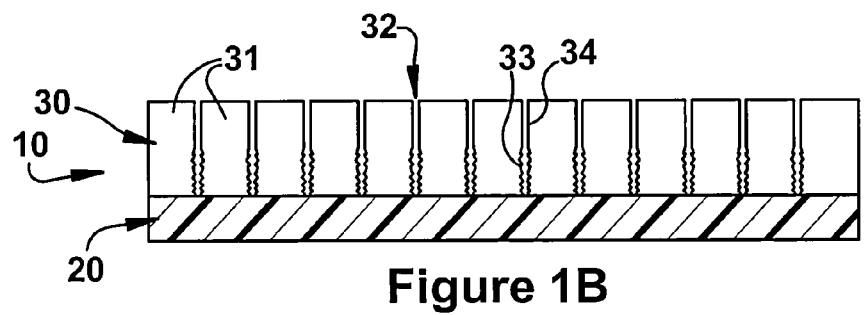
Figure 1C:
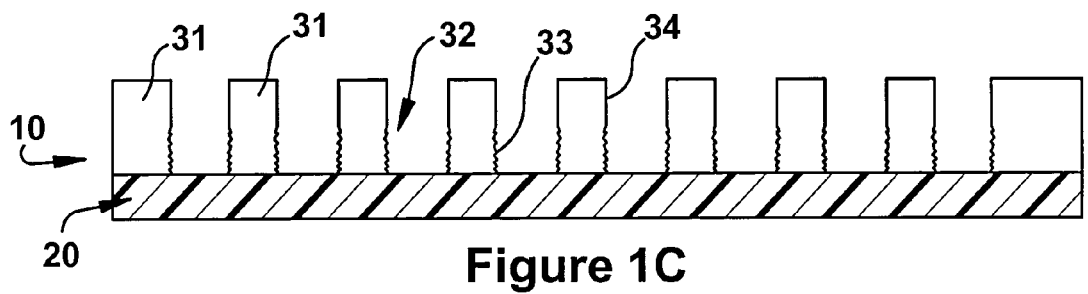

Referring now to the drawings, and initially to FIGS. 1A-1C, an elastic laminate 10 is shown. The elastic laminate 10 comprises an elastic layer 20 and a fabric layer 30. The first fabric layer 30 is divided into fabric segments 31 by interruptions 32 which extend through the fabric thickness. The fabric segments 31 diverge in the cross direction C upon laminate elongation (FIG. 1C) and converge in the cross direction C upon laminate recovery (FIG. 1B).

Figure 2A:
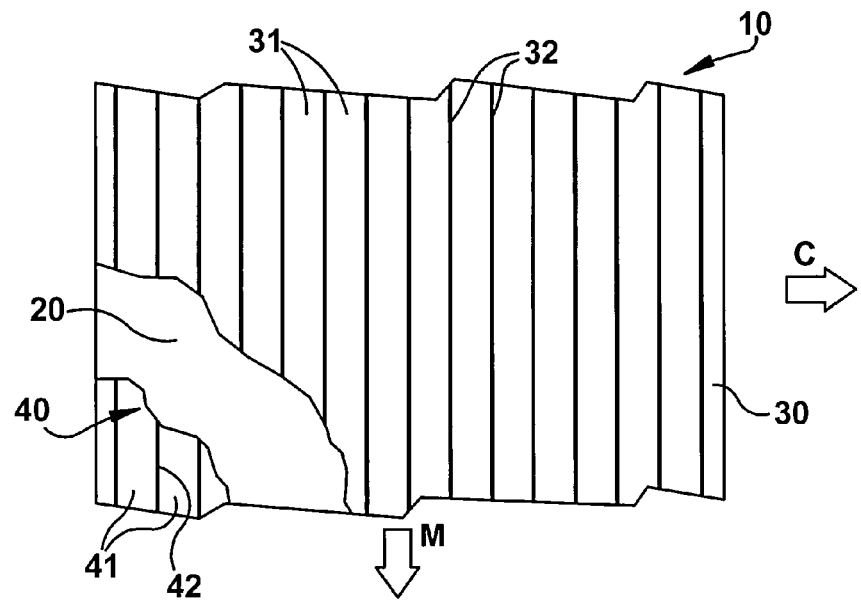
FIGS. 2A-2C are a plan view and side views of an elastic laminate comprising an elastic layer and two fabric layers, the laminate being shown in a relaxed state in FIGS. 2A and 2B, and in an elongated state in FIG. 2C.
Figure 2B:
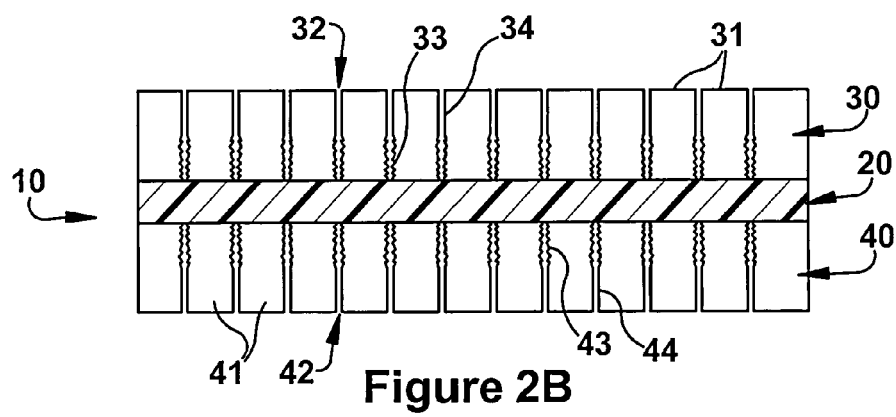
Figure 2C:
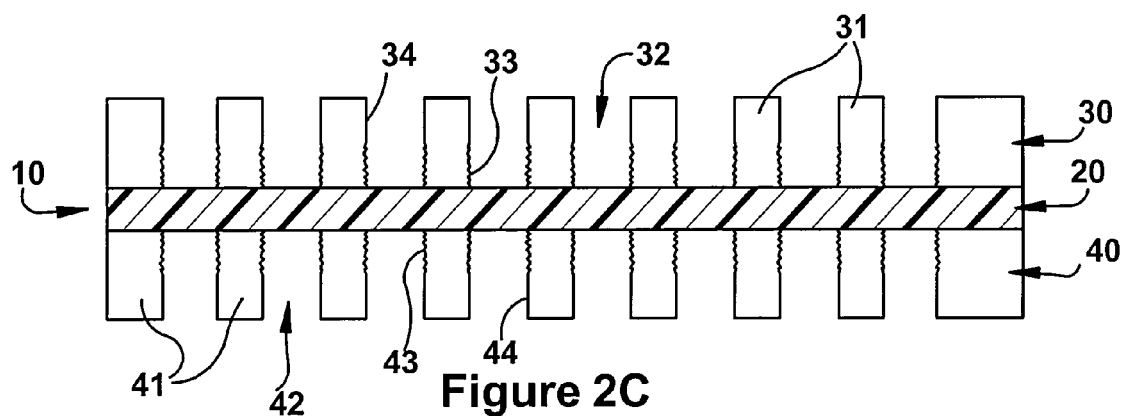

As shown in FIGS. 2A-2C, the elastic laminate 10 can also include a second fabric layer 40, with the elastic layer 20 sandwiched between it and the first fabric layer 30. The second fabric layer 40 can also be divided into diverging/converging fabric segments 41 by interruptions 42. The elastic layer 20 may be hidden by the converged fabric segments 31/41 and/or may be visible between the diverged fabric segments 31/41.

The thicknesses of the layers 20/30/40 are greatly exaggerated in the drawings for ease of explanation. The thicknesses of these layers will usually be in the range of, for example, about 2.5 micrometers to about 100 micrometers or more. If these thicknesses were drawn to scale with the illustrated lengths, it would be difficult to decipher and/or number the layers. Also, neighboring laminate layers will generally be positioned flush against each other, even though some of the figures may give the impression that certain aligned layer sections and/or areas are separated by spaces or gaps and do not contact one another. On this same note, interruptions 32/42 are schematically shown as being rather large in the drawings. While large and/or widely-spaced interruptions 32/42 are not outside the realm of possibility, much smaller spacing is generally excepted. The interruptions 32/42 can be spaced (evenly or unevenly), for example, between 1 mm to 10 mm apart (e.g., about 2 mm, about 3 mm, about 4 mm, about, 5 mm, etc.) along the laminate.

The elastic layer 20 is made of an elastic material that has recoverable elongation properties in a direction C which is cross (e.g., substantially perpendicular) to the machine direction M. The elastic layer 20 can comprise an elastomer selected from the group consisting of styrene block copolymers, polyurethanes, polyesters, polyethers, and polyether block copolymers. Additionally or alternatively, the elastic layer 20 can comprise a vinyl arene-containing block copolymer (e.g., a block copolymer comprising SBS and/or SEBS). The term "elastic" (or related terms such as "elasticized" and "elasticity") means that the layer tends to recover to or near its original size and shape after removal of a force causing a deformation. For example, an elastic material or composite can be elongated by at least 50% of its relaxed length and will recover, upon release of the applied force, at least 40% of its elongation. For example, the elastic layer 20 can be capable of being elongated by at least 100% to 300% of its relaxed length and can recover, upon release of an applied force, at least 25% to 50% of its elongation.

The first fabric layer 30 and/or the second fabric layer 40 can be a nonelastic layer and, more particularly, a nonwoven nonelastic layer. If the fabric layers 30/40 are nonwoven layers (e.g., nonelastic nonwoven layers), they can be, for example, polyolefin, such as polyethylene and/or its copolymers, or polypropylene and/or its copolymers, or mixtures of the aforementioned polyolefins, polyurethanes, polyester, polyether or polymide. The nonwoven materials can comprise, for example, spunbonded webs, meltblown webs, air laid layer webs, bonded carded webs, hydroentangled webs, wet-formed webs or any combination thereof. The nonwoven layers can have a weight of about 10 gsm to about 100 gsm and the layers 30/40 can vary in weight.

The layers 30/40 can be fabric monolayers, that is a single layer of fabric rather than a laminate of a plurality of sublayers. For example, a monolayer structure wherein fibers or other filaments are fused or otherwise integrated into a single substrate layer, can be employed. While monolayer constructions will be preferred in many situations, the layers 30/40 could alternatively have a multilayer construction (i.e., a compilation or lamination of layers wherein different layers are distinguishable and/or separable).

Figure 3A:
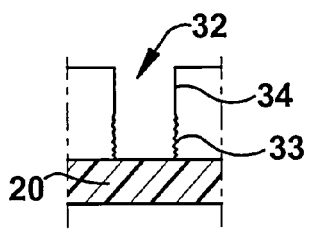
FIGS. 3A-3U are each close-up views of an interruption in the first fabric layer and/or the second fabric layer.
Figure 3B:
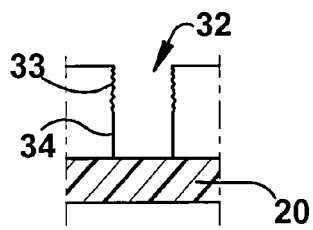
Figure 3C:
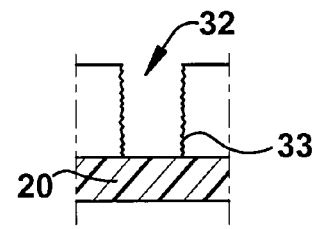
Figure 3D:
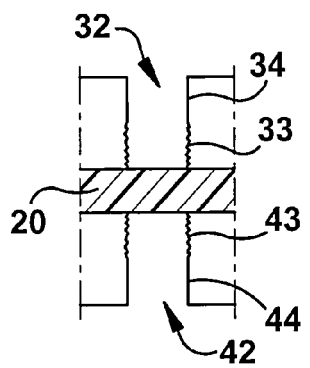
Figure 3E:
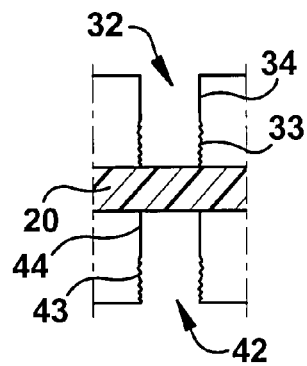
Figure 3F:
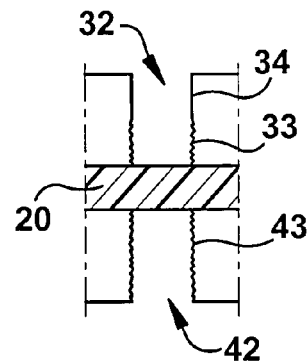
Figure 3G:
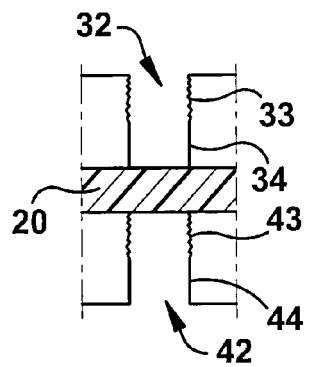
Figure 3H:
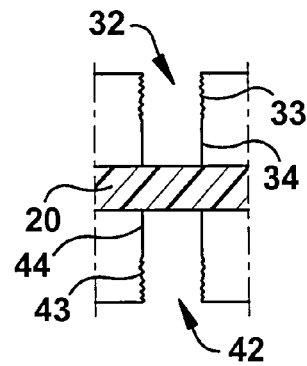
Figure 3I:
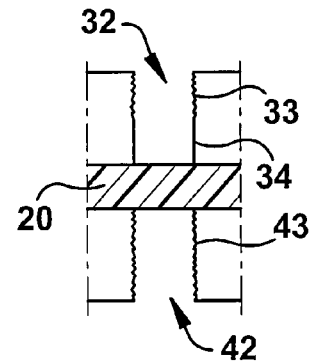
Figure 3J:
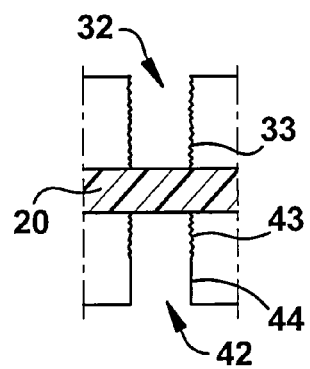
Figure 3K:
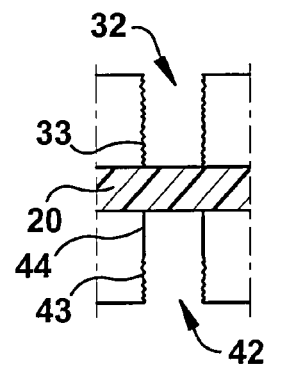
Figure 3L:
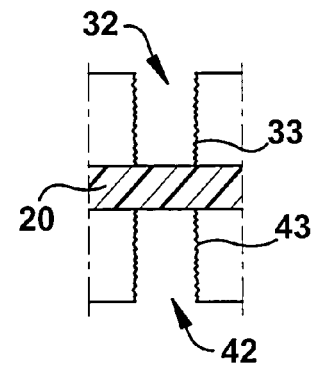
Figure 3M:
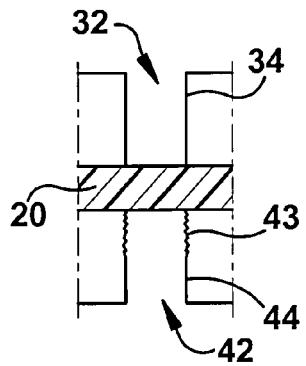
Figure 3N:
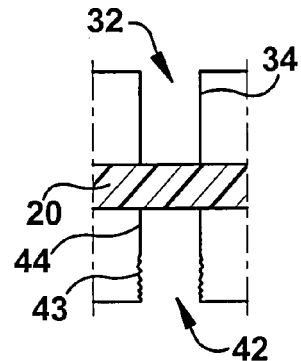
Figure 3O:
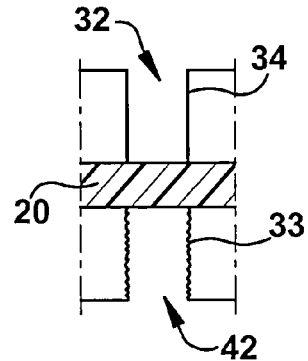
Figure 3P:
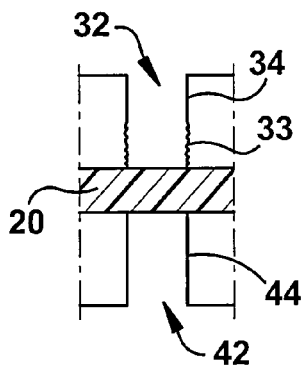
Figure 3Q:
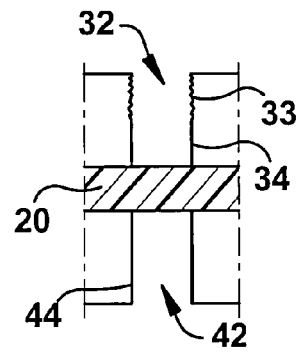
Figure 3R:
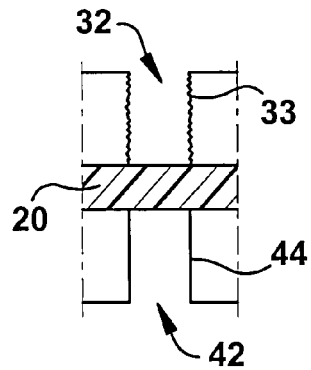
Figure 3S:
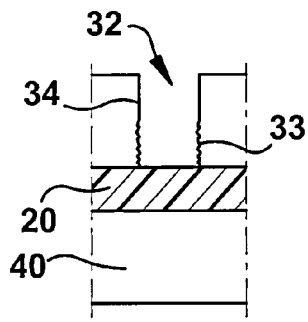
Figure 3T:
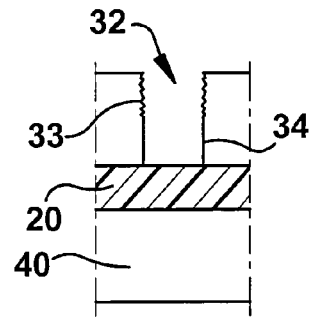
Figure 3U:
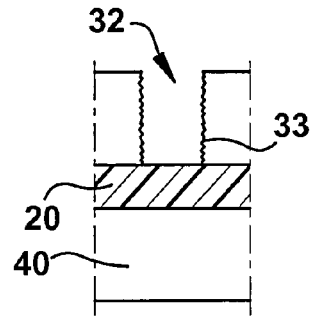

If the elastic layer 20 is used as a reference layer, the fabric layer 30 and the fabric layer 40 will each have a proximal side located closest to the elastic layer 20 and a distal side located away therefrom. The thickness of the fabric layer 20/30 is the distance between its proximal and distal sides. Consequently, as shown in FIGS. 3A-3U, the interruptions 32/42 can be viewed as each having a proximal region 33/43 and a distal region 34/44. If one fabric layer is elastic (e.g., the second fabric layer 40), interruptions may not be necessary in this layer (see FIGS. 3S-3U).

As is explained in more detail below, the fabric segmenting steps comprise applying a series of discrete rupture-inducing forces to form the proximal interruption regions 33 of the first fabric 30 (FIGS. 3A, 3C-3F, 3J-3L, 3P, 3R, and 3S), the distal regions 34 of the first fabric 30 (FIGS. 3B, 3C, 3G-3L, 3Q, 3R, 3T and 3U), the proximal regions 43 of the second fabric 40 (FIGS. 3D, 3F, 3G, 3I, 3J, 3L, 3M, and 3O), and/or the distal regions 44 of the second fabric 40 (FIGS. 3E, 3F, 3H, 3I, 3K, 3L, 3N, and 3O). Both interruption regions 33/34 of the first fabric 30 can be ruptured regions (FIGS. 3J-3L, 3R and 3U) and/or both interruption regions 43/44 of the second fabric 44 can be ruptured regions (FIGS. 3F, 3I, 3L, and 3O).

The non-ruptured interruption regions 33/43 can be die-cut, kiss-cut, slit, scored, laser-cut, ultrasound-cut, or otherwise sharply severed. Thus, the first fabric's proximal interruption region 33 (FIGS. 3B, 3G-3I, 3M-3O, 3Q and 3T), the first fabric's distal interruption region 34 (FIGS. 3A, 3D-3F, 3M-3P, and 3S), the second fabric's proximal interruption region 43 (FIGS. 3E, 3H, 3K, 3N, 3P, 3Q, and 3R), and/or the second fabric's distal interruption region 44 (FIGS. 3D, 3G, 3J, 3M, 3P, 3Q, and 3R), can be formed in this manner. Such a severing step can be employed on the first fabric 30 when the rest of the interruption 32 is ruptured (FIGS. 3A, 3B, 3D-3I, 3P, 3Q, 3S, and 3T) and can be employed on the second fabric 40 when the rest of the interruption 42 is ruptured (FIGS. 3D, 3E, 3G, 3H, 3J, 3K, 3M and 3N). The first fabric's interruption 32 can have both regions 33/34 severed (FIGS. 3M-3O) or the second fabric's interruption 42 can have both regions 43/44 severed (FIGS. 3P-3R).

Figure 4A:
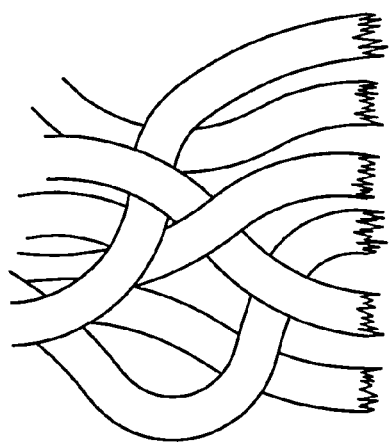
FIGS. 4A and 4B are schematic magnified representations of a ruptured interruption region and a severed interruption region, respectively.
Figure 4B:
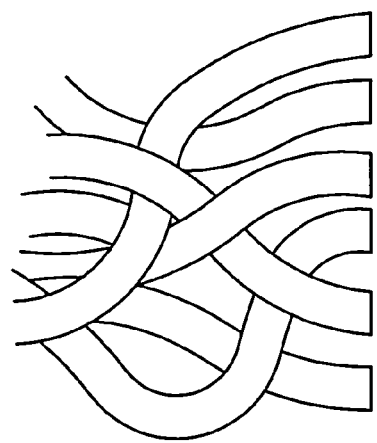
Figure 5A:
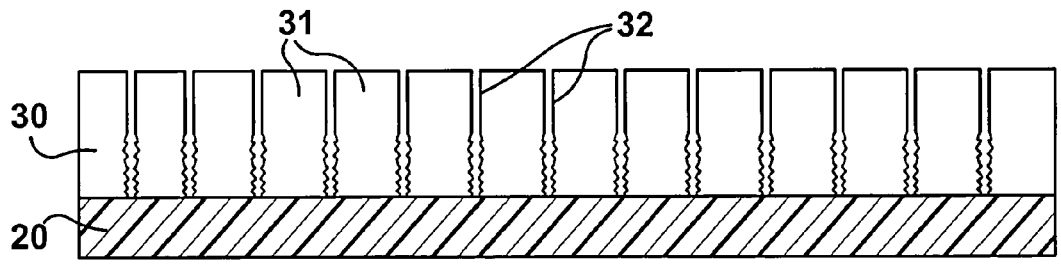
FIGS. 5A-5O and FIGS. 6A-6O are side views of some possible layer and/or interruption arrangements.
Figure 5B:
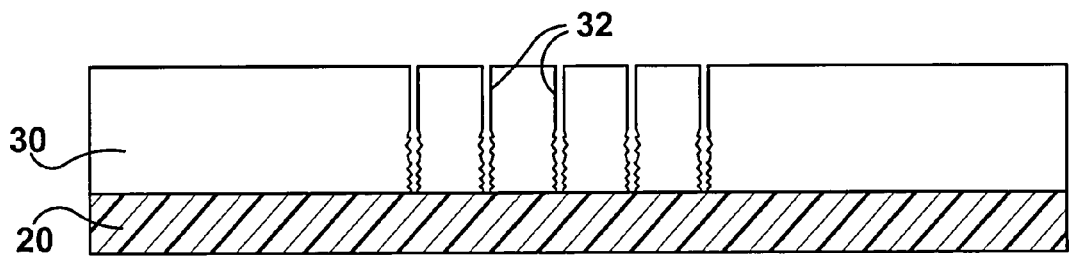
Figure 5C:
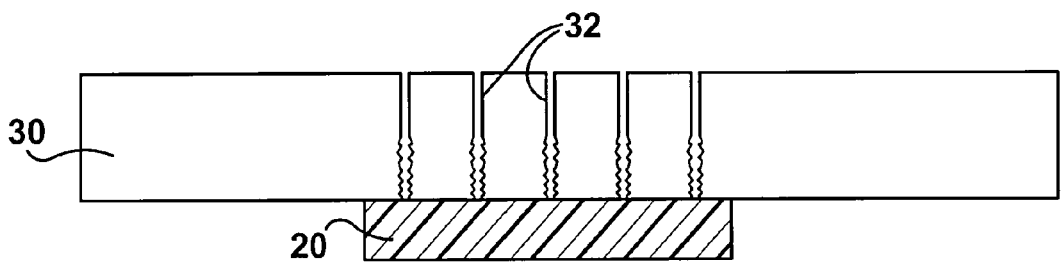
Figure 5D:
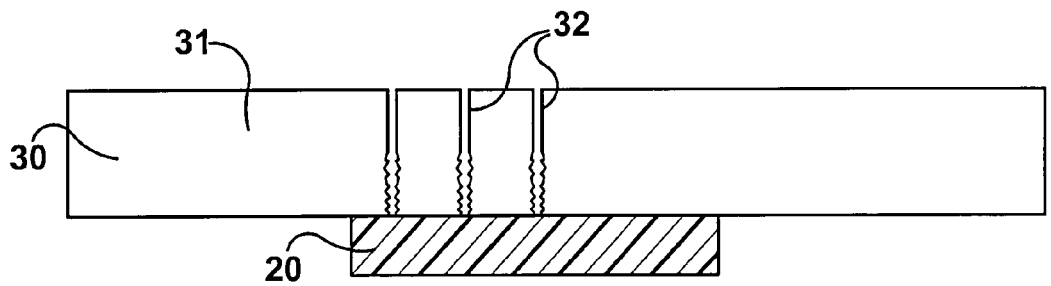
Figure 5E:
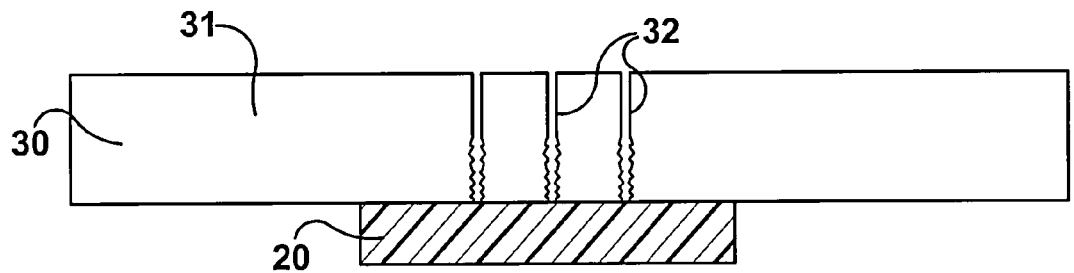
Figure 5F:
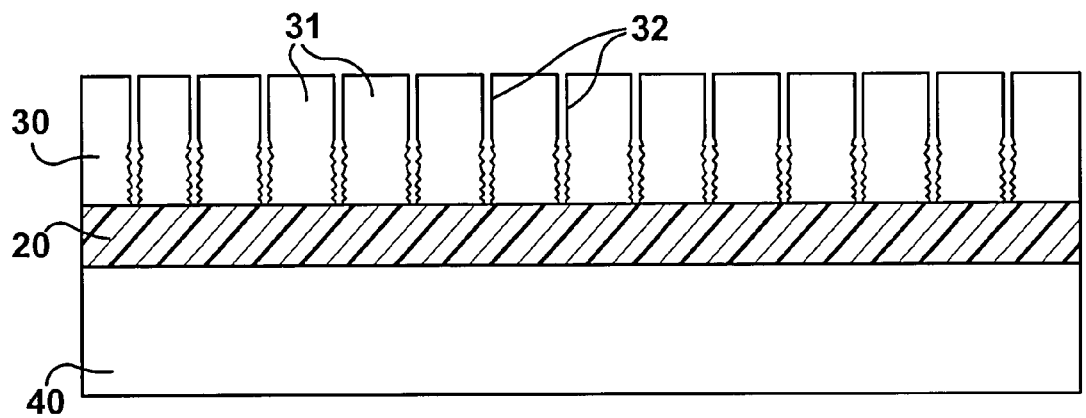
Figure 5G:
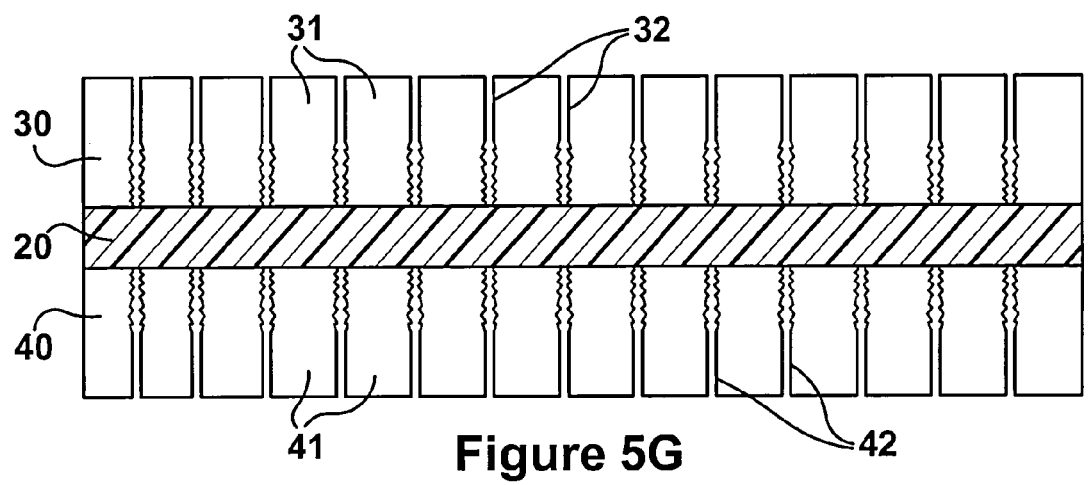
Figure 5H:
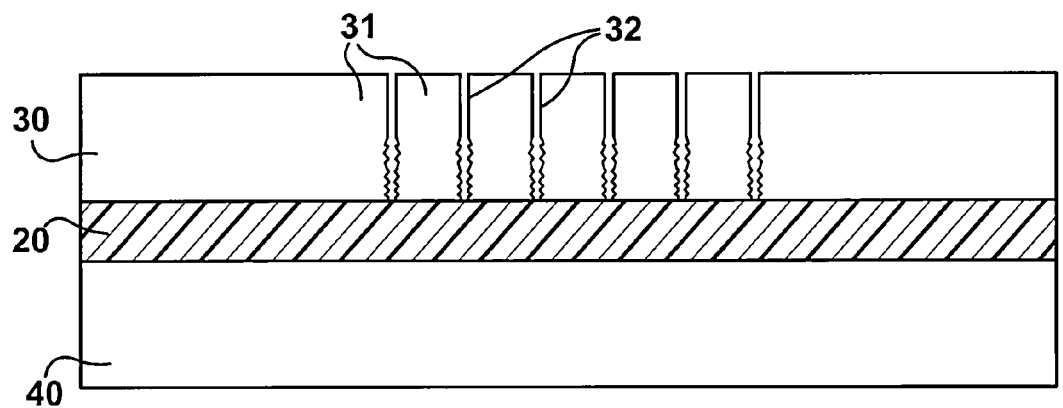
Figure 5I:
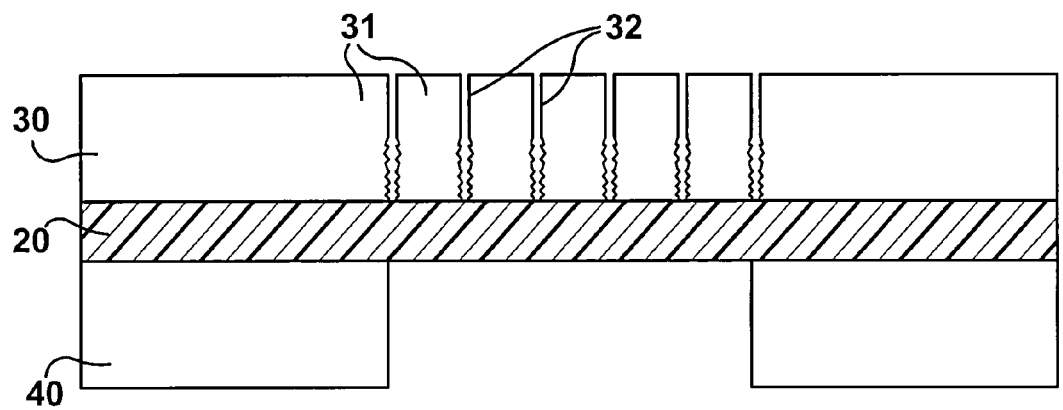
Figure 5J:
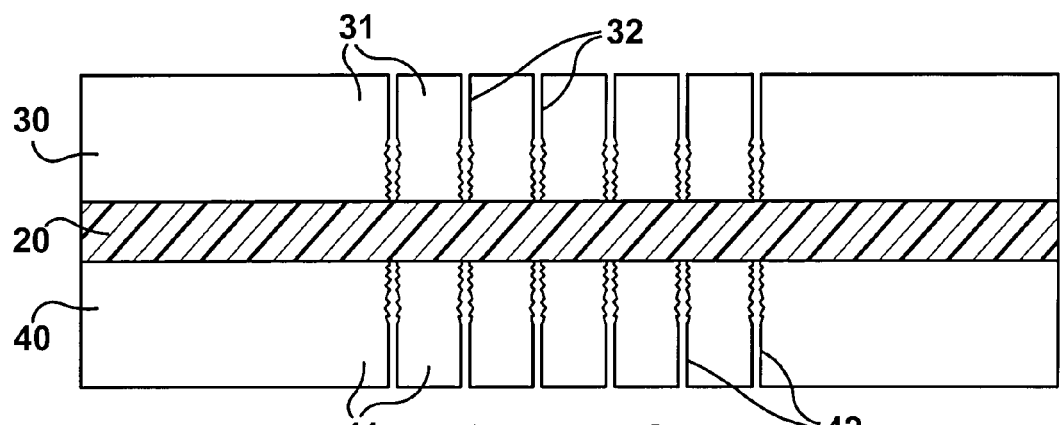
Figure 5K:
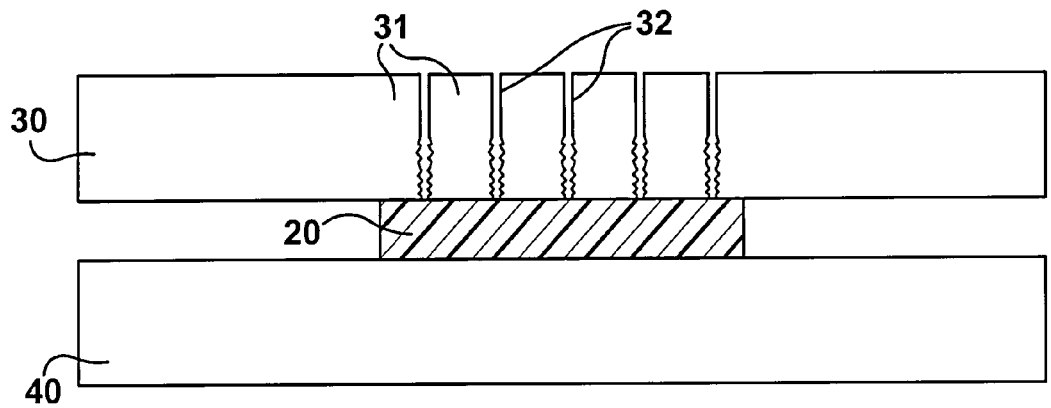
Figure 5L:
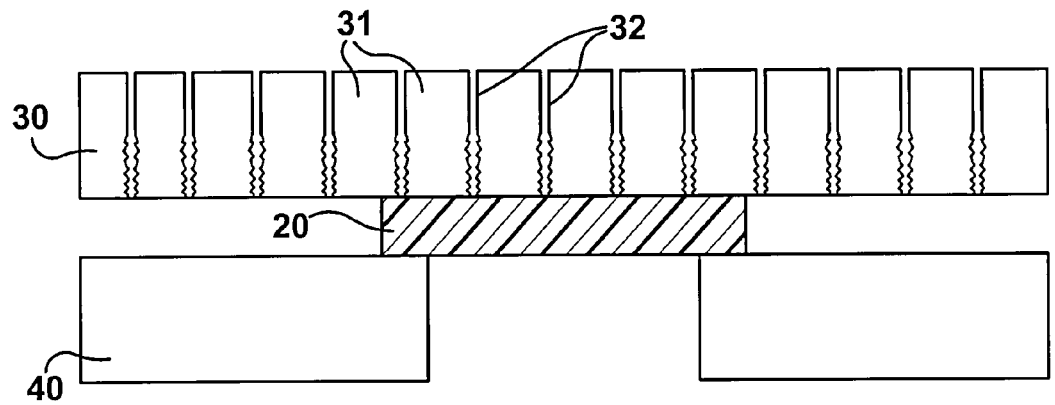
Figure 5M:
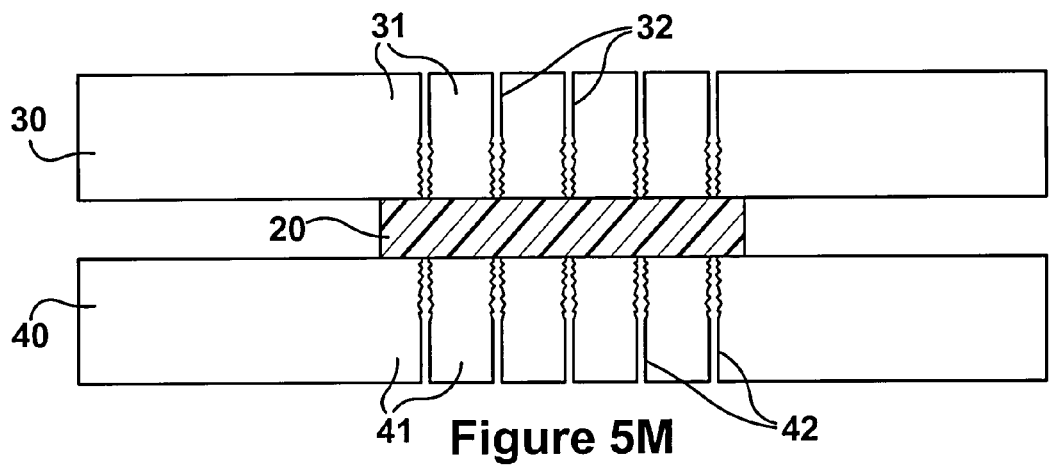
Figure 5N:
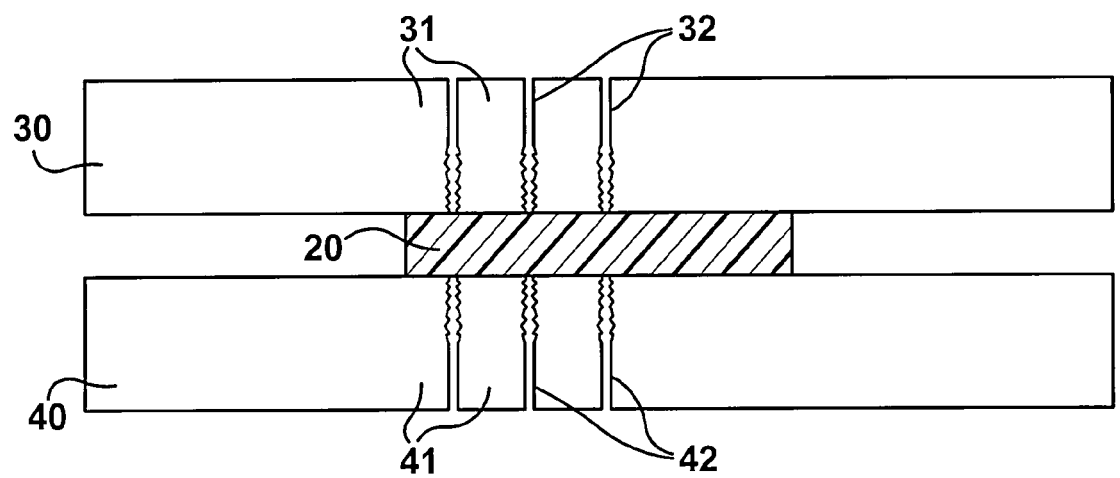
Figure 5O:
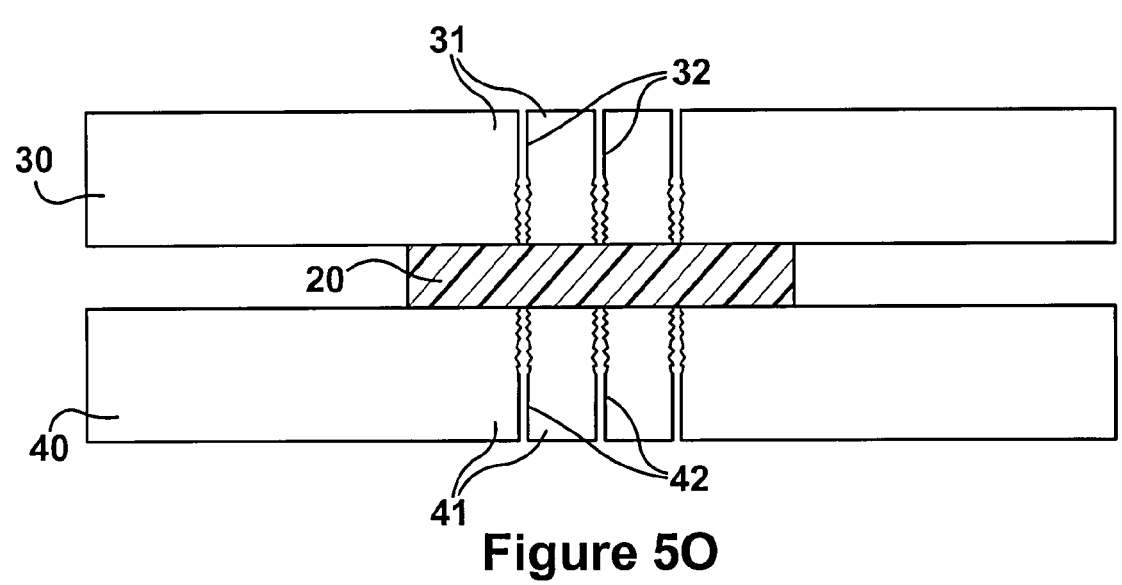
Figure 6A:
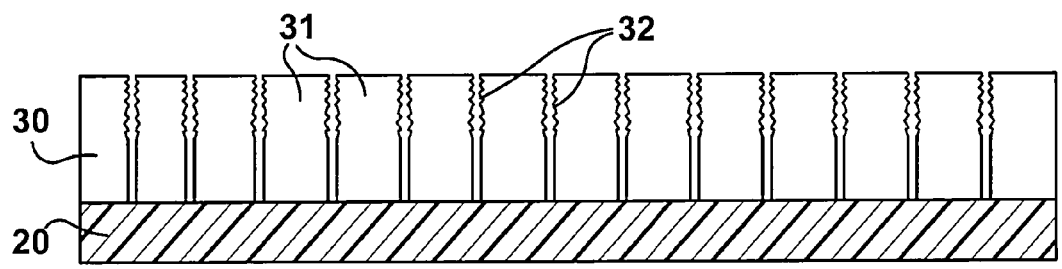
Figure 6B:
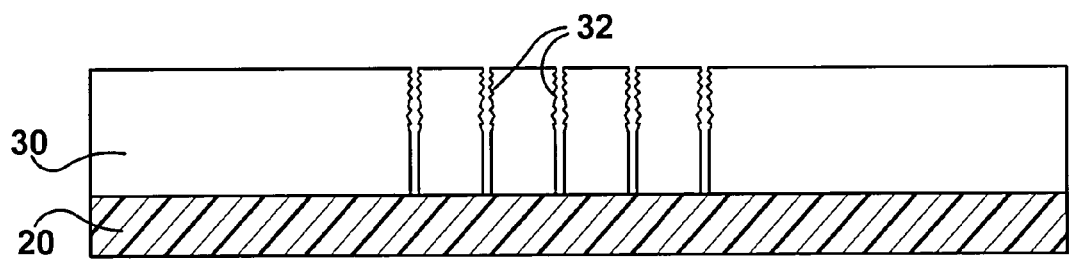
Figure 6C:
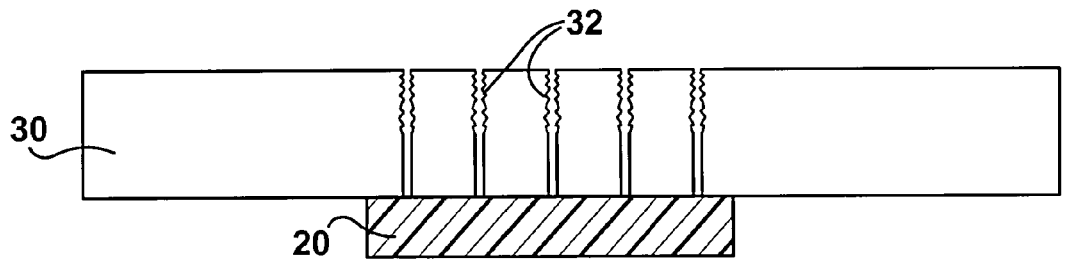
Figure 6D:
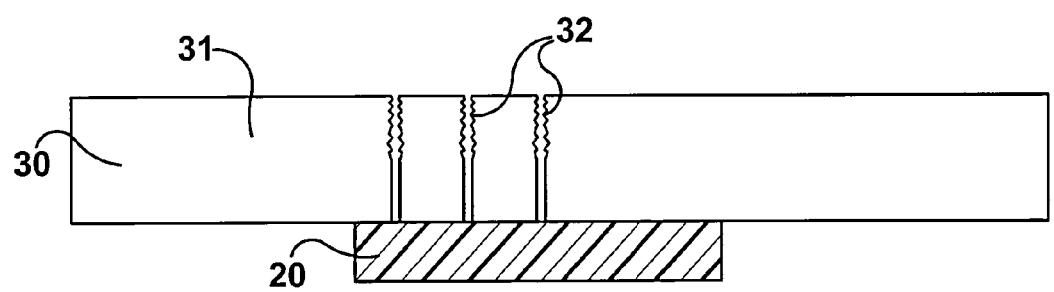
Figure 6E:
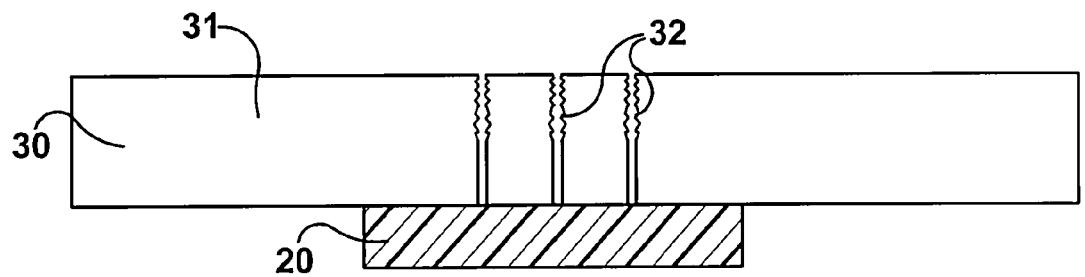
Figure 6F:
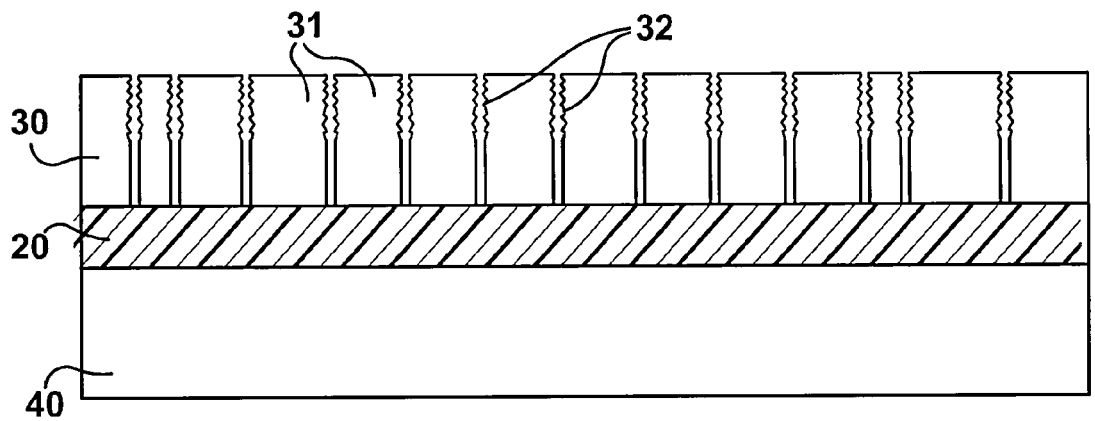
Figure 6G:
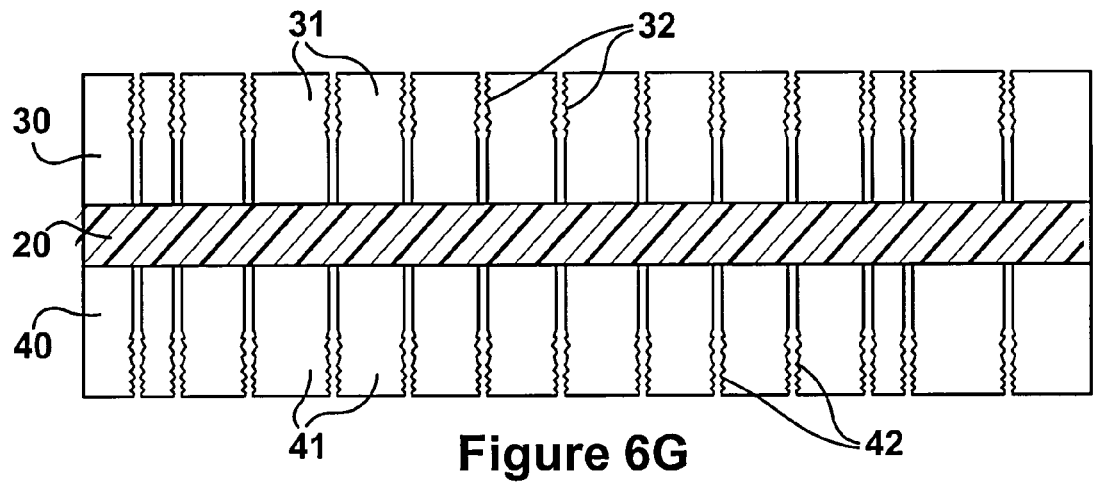
Figure 6H:
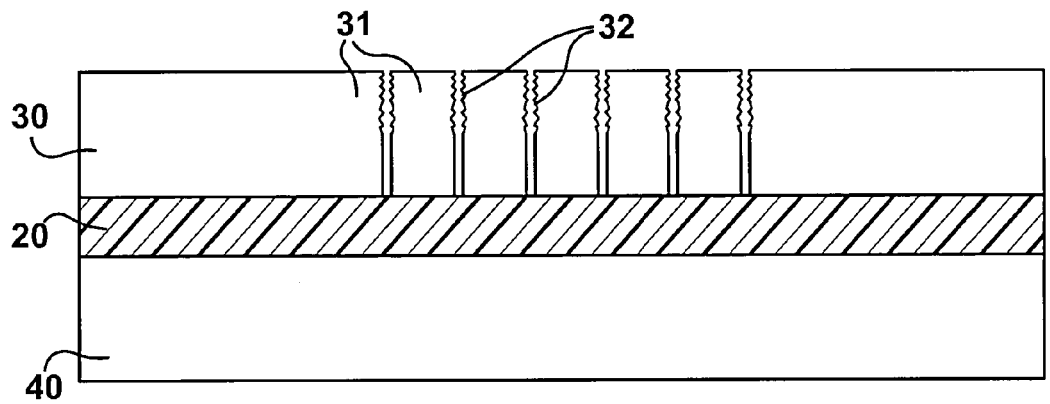
Figure 6I:
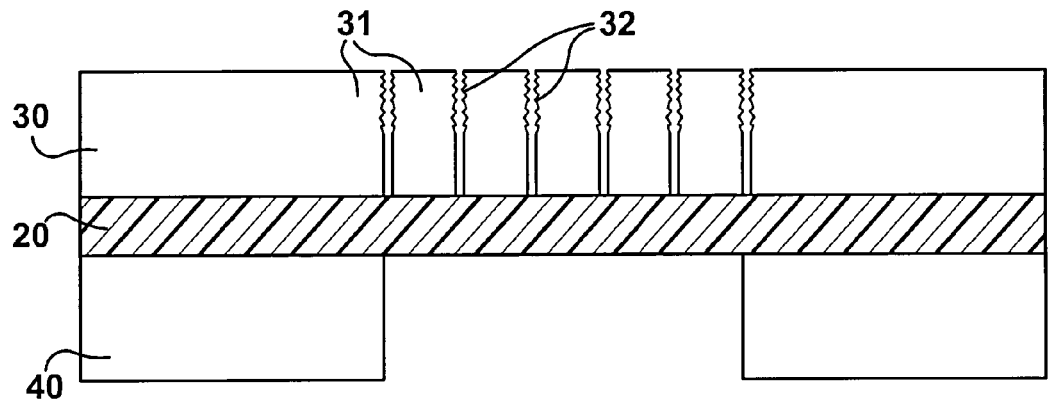
Figure 6J:
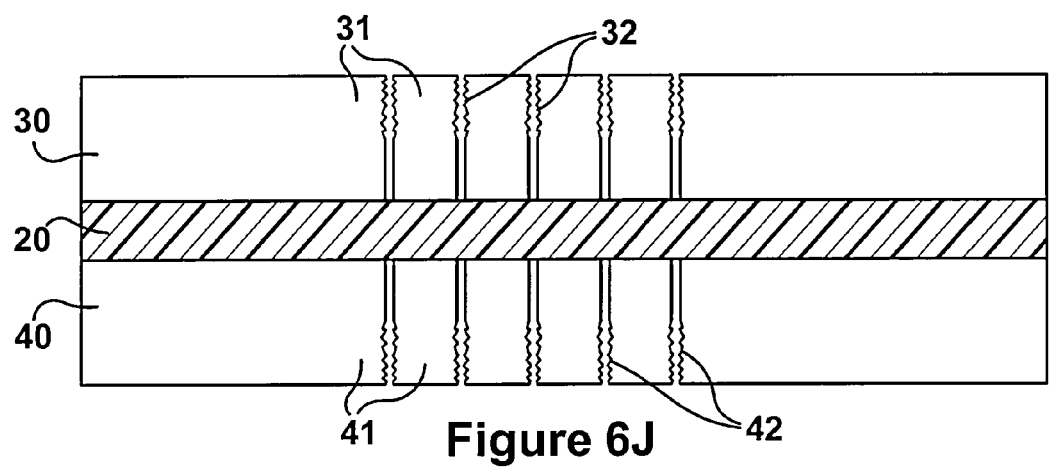
Figure 6K:
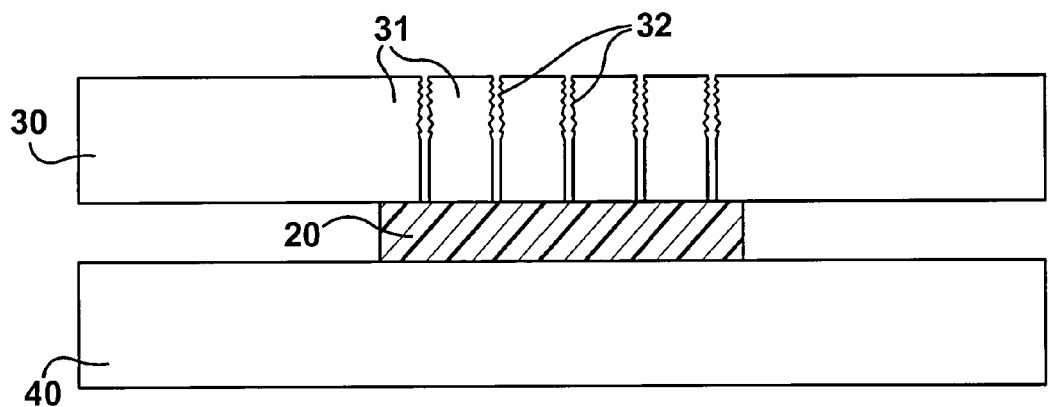
Figure 6L:
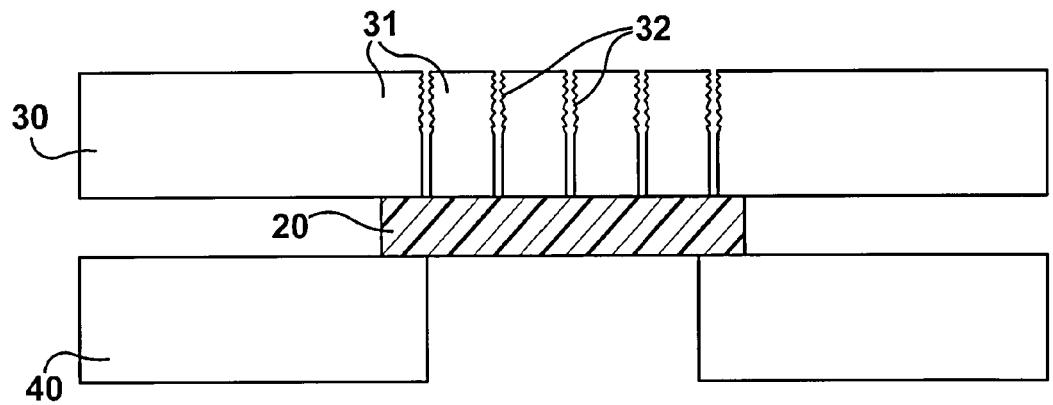
Figure 6M:
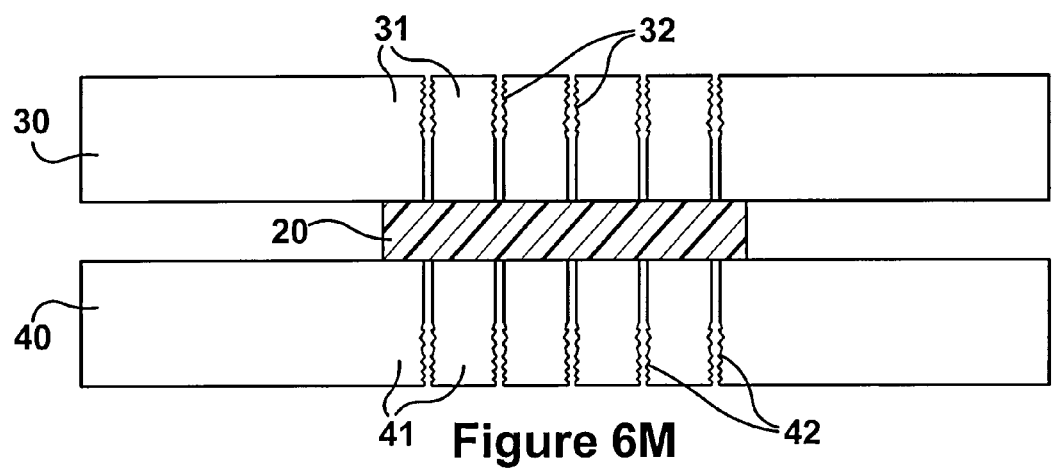
Figure 6N:
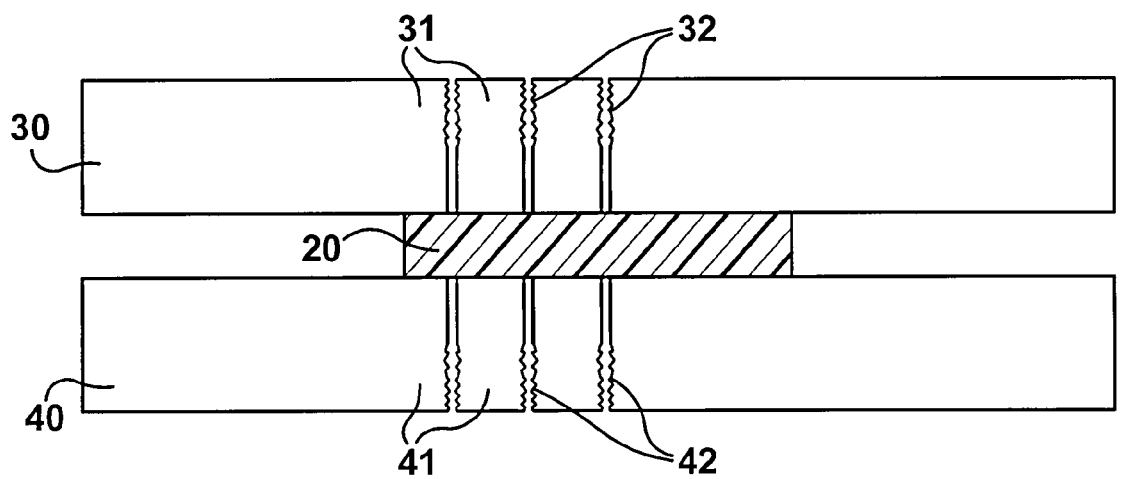
Figure 6O:
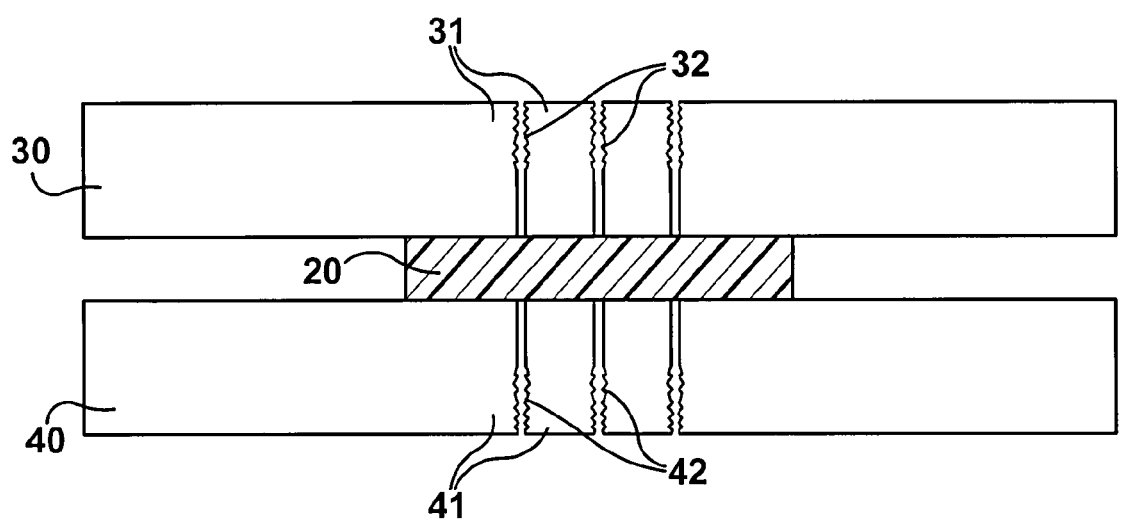

The ruptured regions will be defined by fabric surfaces comprising primarily fractured fabric strand ends, that is fabric strand ends which have been broken roughly and/or unevenly. (See FIG. 4A.) In comparison, the cut (e.g., die-cut, kiss-cut, laser-cut, ultrasound-cut), slit, and/or scored regions will be defined by primarily severed fabric strand ends, that is fabric strand ends which have been severed cleanly and neatly. (See FIG. 4B.) Thus, if an interruption 32/42 is inspected under sufficient magnification, the formation of an interruption region (e.g., ruptured vs. severed) should be determinable.

Turning now to FIGS. 5A-5O and 6A-6O, some possible layer and/or interruptions arrangements are shown. The elastic layer 20 can be coextensive with the first fabric layer 30 (FIGS. 5A, 5B, 5F, 5G, 5H, 5I and 5J, and FIGS. 6A, 6B, 6F, 6G, 6H, 6I and 6J) or this layer 20 can be non-coextensive with first fabric layer 30 (FIGS. 5C, 5D, 5E, 5K, 5L, 5M, 5N and 5O, and FIGS. 6C, 6D, 6E, 6K, 6L, 6M, 6N and 6O). The second fabric layer 40 can be coextensive with the first fabric layer 30 (FIGS. 5F, 5G, 5H, 5J, 5K, 5M, 5N and 5O, and FIGS. 6F, 6G, 6H, 6J, 6K, 6M, 6N and 6O) or non-coextensive with the first fabric layer 30 (FIGS. 5I and 5L, and FIGS. 6I and 6L). The interruptions 32/42 can be coextensive with their fabric layer 30/40 (FIGS. 5A, 5F, 5G and 5L, and FIGS. 6A, 6F, 6G, and 6L) or can be non-coextensive therewith (FIGS. 5B, 5C, 5D, 5E, 5H, 5I, 5J, 5K, 5M, 5N and 5O, and FIGS. 6B, 6C, 6D, 6E, 6H, 6I, 6J, 6K, 6M, 6N and 6O). The interruptions 32/42 can be can be coextensive with the elastic layer 20 (FIGS. 5A, 5B, 5F, 5G, 5K, 5L and 5M, and FIGS. 6A, 6B, 6F, 6G, 6K, 6L and 6M) or they can be non-coextensive with the elastic layer 20 (FIGS. 5D, 5E, 5H, 5I, 5J, 5N and 5O, and FIGS. 6D, 6E, 6H, 6I, 6J, 6N and 6O).

Elastic-coextensive interruption patterns allow full advantage to be taken of the elastic (which is often the most expensive) material. However, when the elastic layer 20 is non-coextensive with the fabric layers 30/40 (FIGS. 5C-5E, 5K, and 5L-5O and FIGS. 6C-6E, 6K and 6L-6O), the post-interruption anchoring of the fabric extensions (i.e., the portions of the fabric not laminated to the elastic layer 20) must also be considered. If the fabric layer 30/40 is segmented outside (or almost outside) the reach of the elastic layer 20, this may destroy the cantilevering connection of the fabric extensions. Thus, it may be desirable for the interruptions to extend almost, but not quite, the full cross-extent of the elastic layer 20 and thereby leave an uninterrupted margin aligned with each lateral edge of the elastic layer 20. Margin widths in the range of 2-20 millimeters, 4 to 12 millimeters, and/or 6 to 10 millimeters, may be sufficient for this purpose, although shorter or longer margins may be more appropriate in certain situations.

Figure 7A:
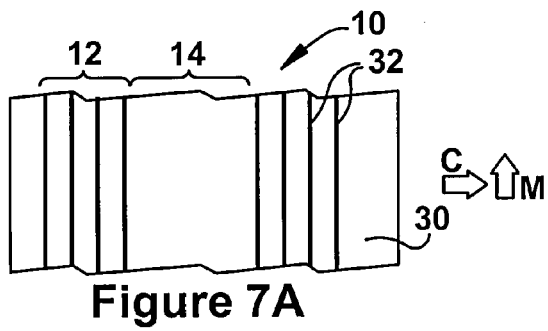
FIGS. 7A-7O are some schematic views showing some possible interruption patterns and/or path-geometries.
Figure 7B:
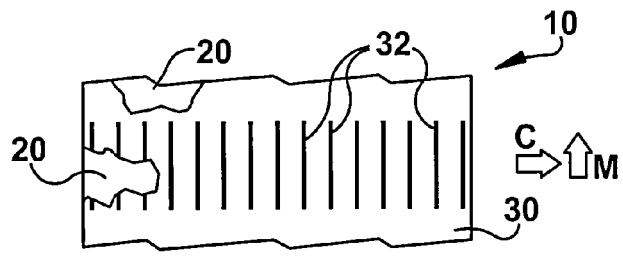
Figure 7C:
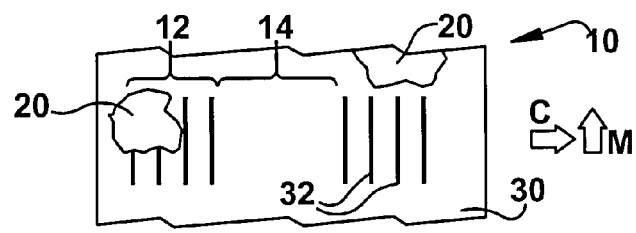
Figure 7D:
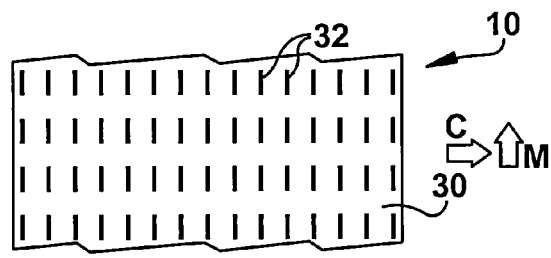
Figure 7E:
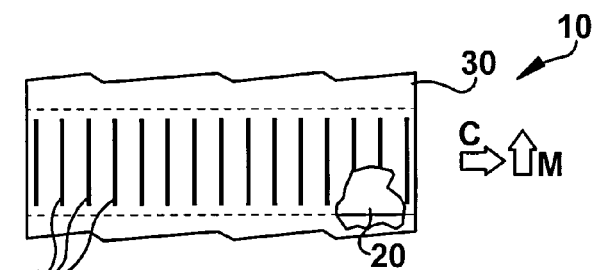
Figure 7F:
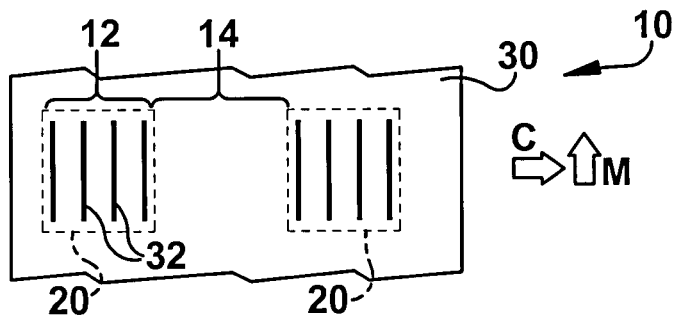
Figure 7G:
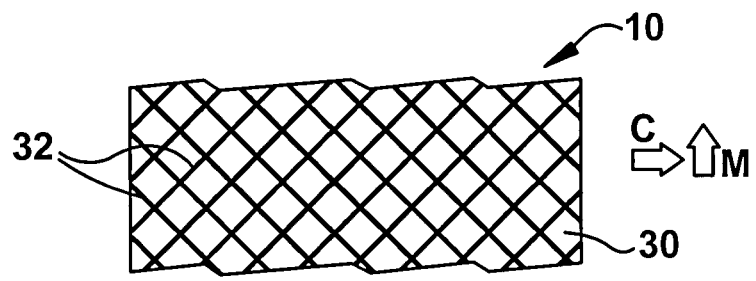
Figure 7H:
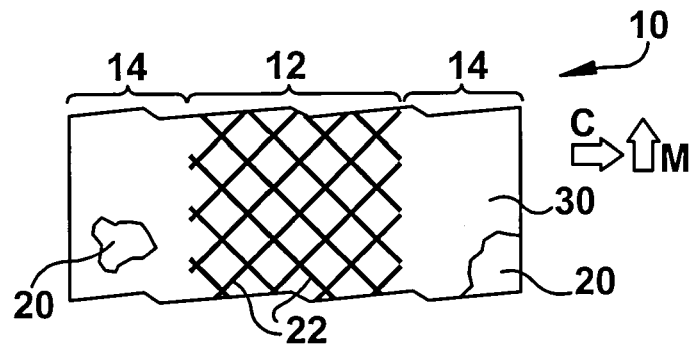

Turning now to FIGS. 7A-7I, some possible layer and/or interruptions arrangements in the machine-direction M are shown. The interruptions 32/42 can extend continuously in the machine direction, but they need not do so (FIGS. 7B, 7C, 7E, 7F, 7H and 7I). The elastic layer 20 can be coextensive with the fabric layer 30/40 in the machine direction M (FIGS. 7A-7D and FIGS. 7G-7I) or the elastic layer 20 can be non-coextensive with the fabric layer 30/40 in the machine direction M (FIG. 7E and FIG. 7F). The interruptions 32/42 can be coextensive with the elastic layer 20 (FIGS. 7D, 7E, 7F and 7I) or the interruptions can be non-coextensive with the elastic layer 20 (FIGS. 7A-7C and FIG. 7H) in the machine direction M.

The interruptions 32/42 can be elongated and extend in a direction non-parallel to the cross direction C. For example, the interruptions 32/42 can extend substantially parallel to the machine direction (FIGS. 7A-7F). Alternatively, the interruptions 32/42 can extend an acute angle (e.g., about 10° to about 75°, about 10° to about 60°, and/or about 10° to about 45°)

relative to the machine direction M (FIGS. 7G-7I) and these interruptions 32/42 can (but need not) intersect. Although not specifically shown in the drawings, the paths of the interruptions 32/42 can include both paths substantially parallel to the machine direction M and paths at an acute angle relative to the machine direction M. The parallel and angularly offset paths can (or cannot) intersect.

Figure 7I:
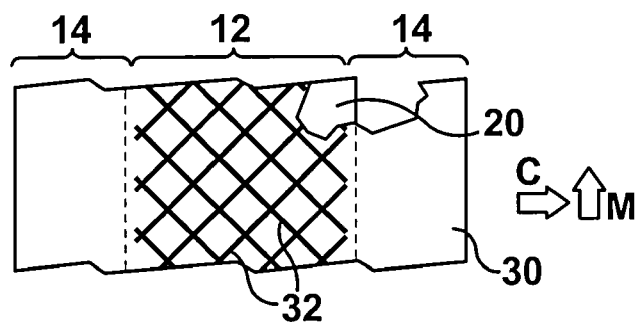
Figure 7J:
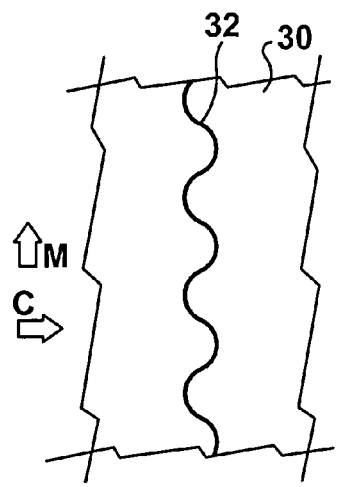
Figure 7K:
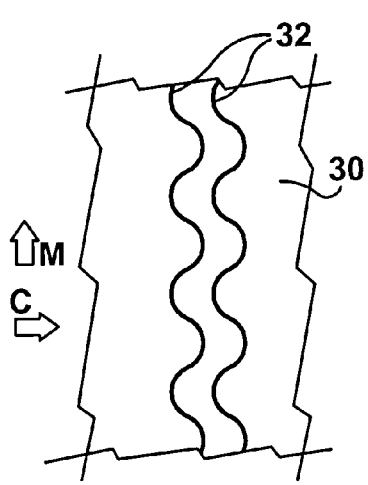

In other words, the laminate 10 can have interrupted zones 12 and uninterrupted zones 14 (with the interruptions 32/42 being located only in the interrupted zones 12). The elastic layer 20 can be coextensive with both the interrupted zones 12 and the uninterrupted zones 14 (FIGS. 7A-7C, and FIG. 7H) or the elastic layer 20 can be substantially coextensive with only the interrupted zones 12 in the cross direction C and/or the machine direction M (FIGS. 7E-7F and FIG. 7I). The earlier option may ease layer compilation steps in certain situations; the latter option may reduce material costs.

Figure 7L:
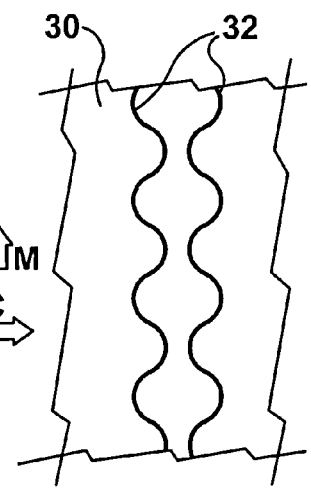
Figure 7M:
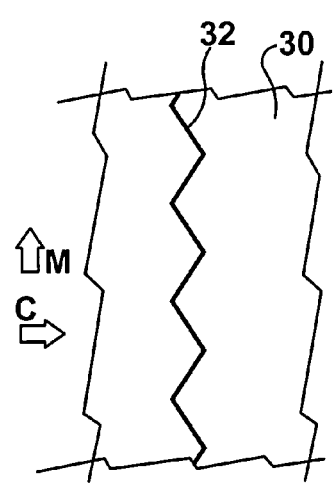
Figure 7N:
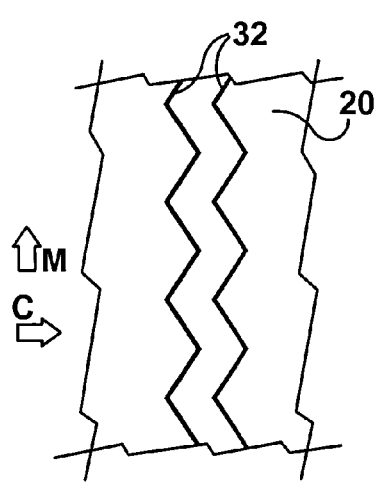
Figure 7O:
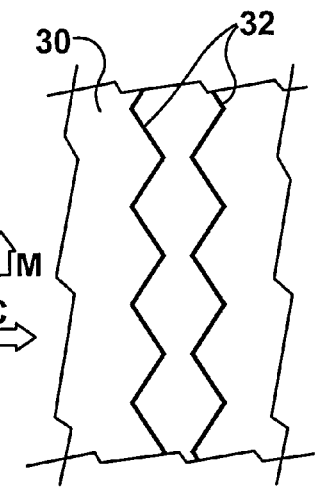

The interruptions 32/42 can follow a straight linear path, however, as shown in FIGS. 7J-7O, the paths need not always be linear. The interruptions 32/42 can follow a sinusoidal path (FIGS. 7J-7L) or a zigzag path (FIGS. 7M-7O), with adjacent interruptions being either aligned with each other (FIGS. 7K and 7N) or offset from each other (FIGS. 7L and 7O). In the case of nonlinear paths, the angle of the interruption 32/42 relative to the machine direction M can be determined by the centerline of the path. That being said, incremental rupturing steps may be more easily and/or effectively performed with the straight and/or uncomplicated path geometries.

Figure 8A:
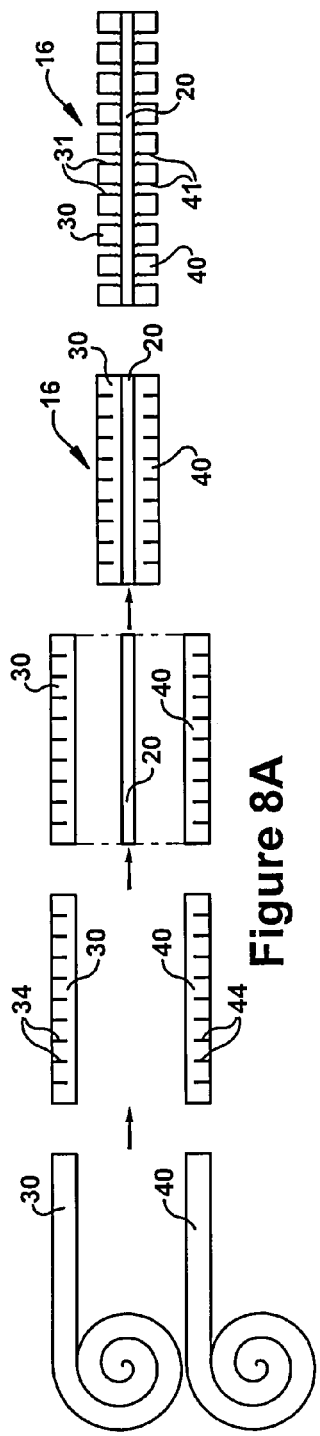
FIGS. 8A-8Y are schematic views of a method of making the elastic laminate.
Figure 8B:
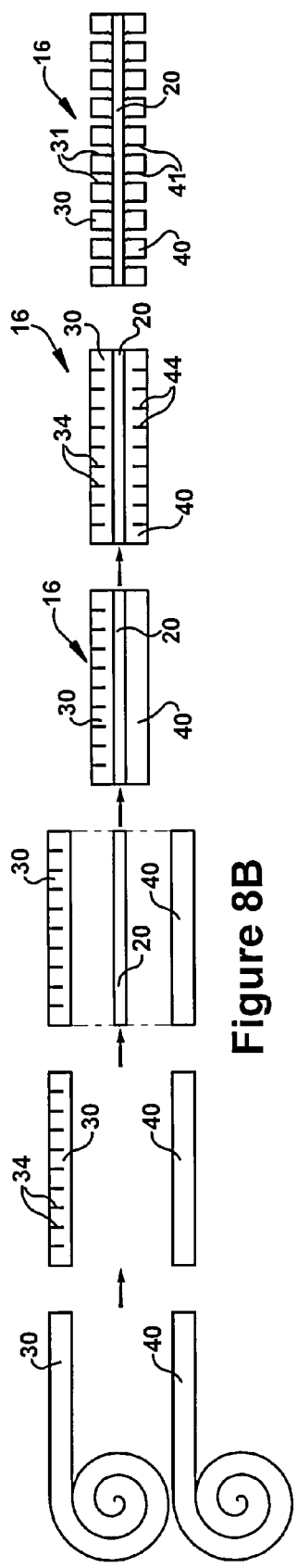
Figure 8C:
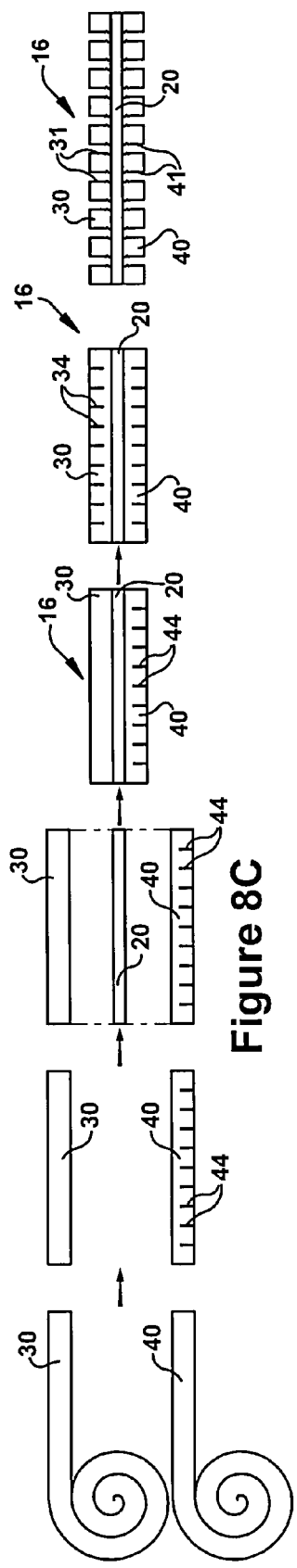
Figure 8L:
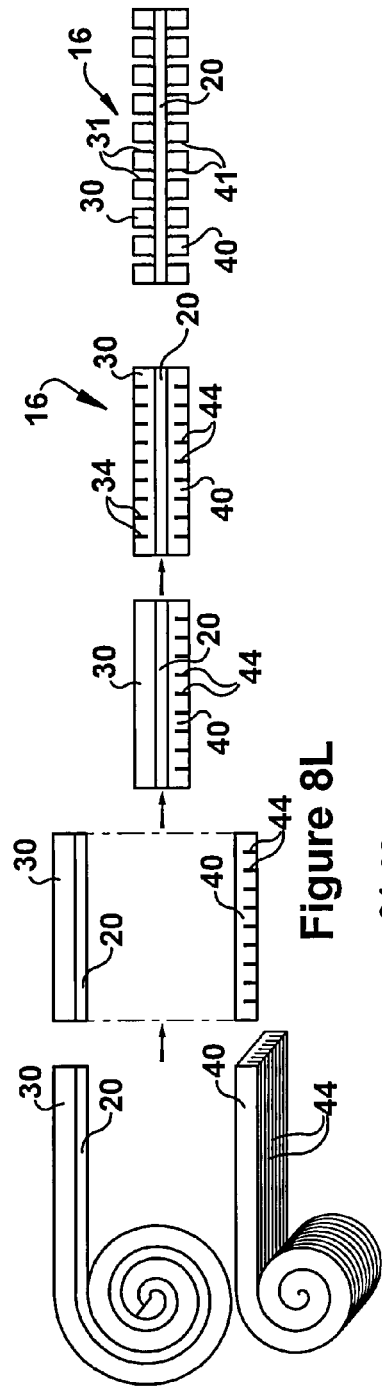
Figure 8M:
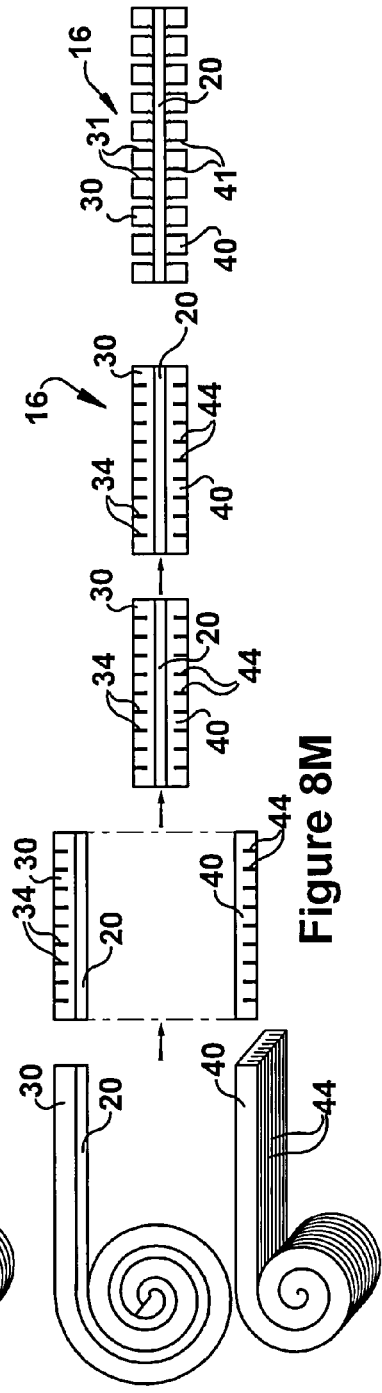
Figure 8N:
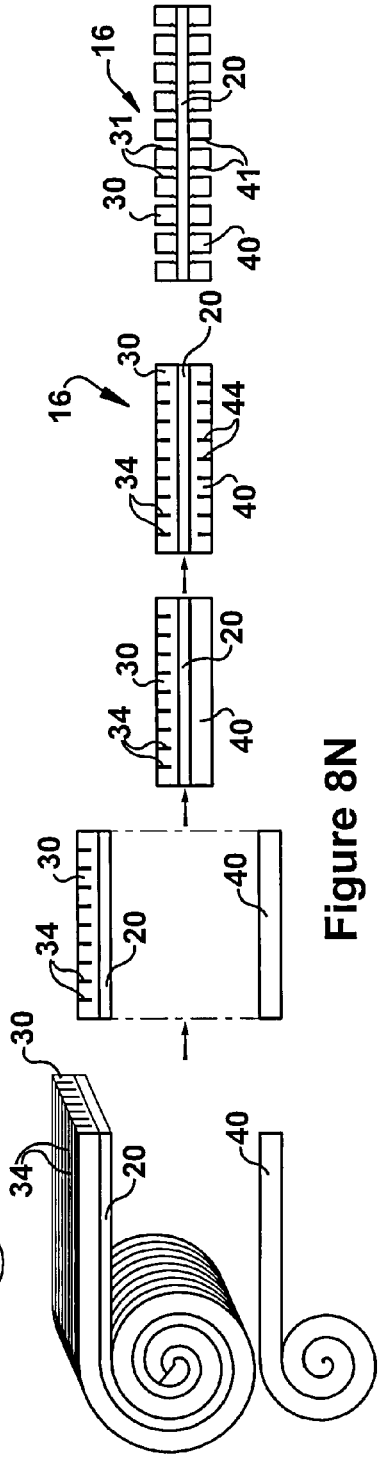

Referring now to FIGS. 8A-8Y, methods of making the elastic laminate 10 are schematically shown. The method generally comprises the steps of forming the severed interruption regions in the fabric layer 30/40, laminating the fabric layers 30/40 to the elastic layer 20, and rupturing the non-severed regions of the interruptions 32/42. The severing and laminating steps can form an intermediate laminate 16 on which the rupturing steps are performed to separate the fabric layers 30/40 into the fabric segments 31/41. If the intermediate laminate 16 includes distal severed regions 34/44 (as shown), the rupturing steps form the proximal interruption regions 33/43. If the intermediate laminate 16 includes proximal severed regions 33/43, the rupturing steps form the distal interruptions regions 34/44. If the elastic laminate 10/16 does not include a second fabric layer 40 (or if this layer 40 is elastic or sectioned), the corresponding second-fabric steps would not be necessary.

One or both of the fabric layers 30/40 can be supplied in a continuous format (e.g., a roll) and thereafter have non-ruptured interruption regions formed thereon (FIGS. 8A-8H, 8I-8O, and 8Q-8W). One or both of the fabric layers 30/40 can be supplied in a continuous format (e.g., a roll) with the non-ruptured interruptions already formed thereon (FIGS. 8E-8H, 8L-8P, and 8U-8Y). The non-ruptured interruption regions can be formed in one or both of the fabric layers 30/40 prior to lamination with the elastic layer 20 (FIGS. 8A-8C, 8E-8H, 8K, 8O, 8R, 8S, 8U-8W) or after such lamination (FIGS. 8B-8D, 8F-8G, 8I-8L, 8N, 8Q, 8S, 8T, 8V, and 8W). The elastic layer 20 can be provided separate from the fabric layers 30/40 (FIGS. 8A-8H) or may be supplied in a continuous format (e.g., a roll) therewith (FIGS. 8I-8Y).

As was indicated above, the non-ruptured interruption regions in the intermediate laminate 16 can be formed by die-cutting, kiss-cutting, slitting, scoring, laser-cutting, ultrasound-cutting, or other suitable techniques wherein the fabric layer 30/40 is sharply severed to form the non-ruptured regions. If these severed regions are formed in the fabric layer 30/40 after lamination (FIGS. 8B-8D, 8F-8G, 8I-8L, 8N, 8Q, 8S, 8T, 8V, and 8W), severing must be done without damaging the elastic layer 20. This may prove difficult with physically-contacting cutting elements, such as blades, knives, or slitting wheels. However, with the use of laser, ultrasound, and/or other more precise cutting procedures, post-laminate formation of the severed interruption regions may be possible and even preferred. For example, with laser cutting, (e.g., where carbon dioxide laser beams are delivered via scanner systems with final focusing optics), the cutting depth can be closely controlled by altering the power of the laser. For this same reason, even pre-lamination formation of the severed interruption regions with laser, ultrasound, or other non-contacting severing techniques may be best if a facility is accommodated with the necessary equipment. If the fabric layer 30/40 has severed proximate regions 33/43 (FIGS. 3B, 3E, 3G-3I, 3K, 3M-3P, 3Q, 3T and 3R), post-lamination severing steps may be tricky or even impractical.

Figure 9A:
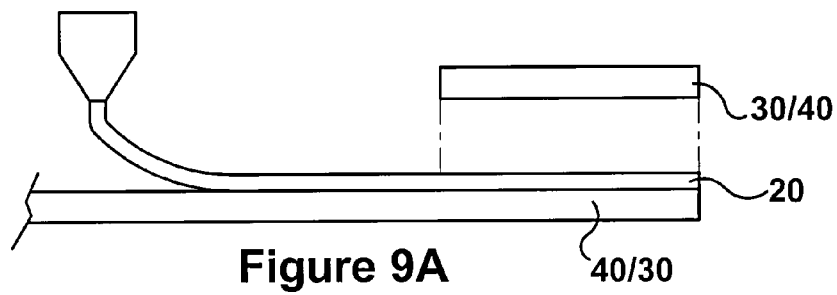
FIGS. 9A-9L are schematic views of some possible techniques for laminating the elastic layer and the fabric layer(s).
Figure 9B:
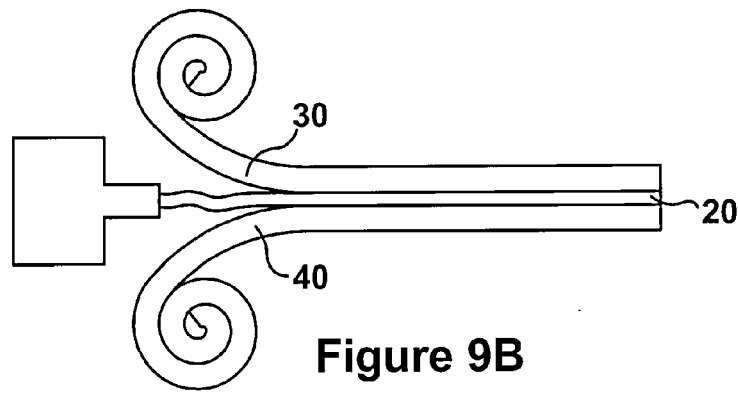

FIGS. 9A-9F show some possible techniques for laminating the fabric layer 30 and/or the fabric layer 40 to the elastic layer 20. One technique is to extrude the elastic layer 20 directly on the fabric layer 30/40 and then laminate the other layer 40/30 thereon (FIG. 9A). Alternatively, the elastic layer 20 can be simultaneously (or substantially simultaneously) extruded onto both the fabric layer 30 and the fabric layer 40 (FIG. 9B). In extrusion techniques, the molten quality of the elastic material will usually be sufficient to bond the fabric layers 30/40 to the elastic layer 20 (or sublayer 22) during lamination.

Figure 9C:
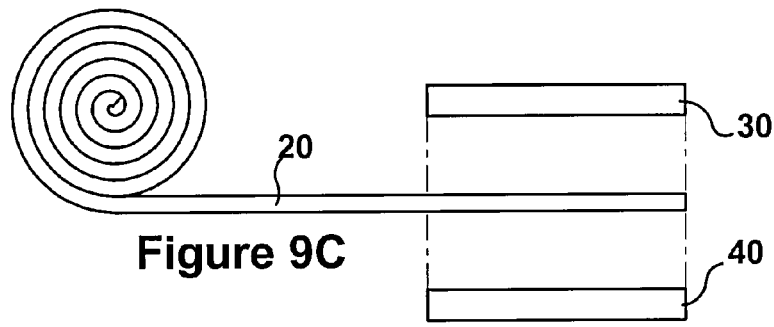
Figure 9D:
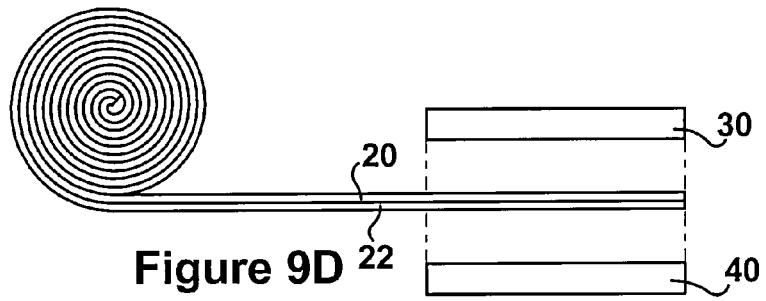
Figure 9E:
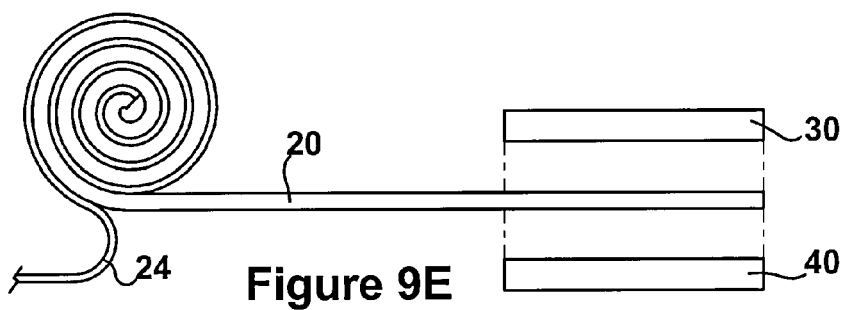
Figure 9F:
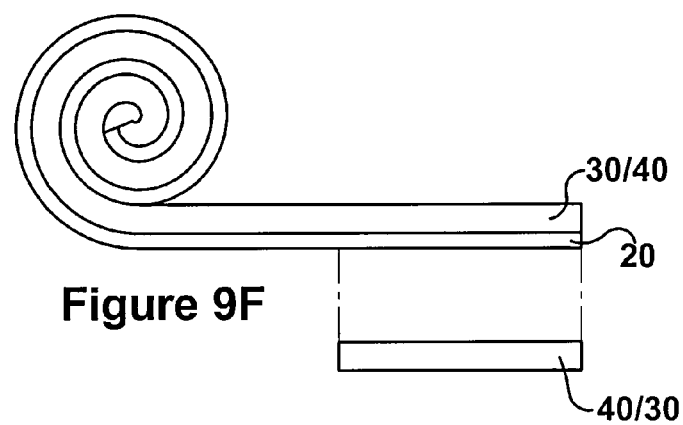

The elastic layer 20 can be provided as a pre-formed film in a continuous roll for lamination to the fabric layers 30/40 (FIGS. 9C-9F). With certain formulations, the layer 20 can be provided as monolayer (FIG. 9C). Otherwise, film-to-film contact may cause blocking unless the elastic layer 20 has skin (or thin fabric) sublayer 22 (FIG. 9D), a liner 24 (FIG. 9E), or is prelaminated to one of the fabric layers 30/40 (FIG. 9F).

Figure 9G:
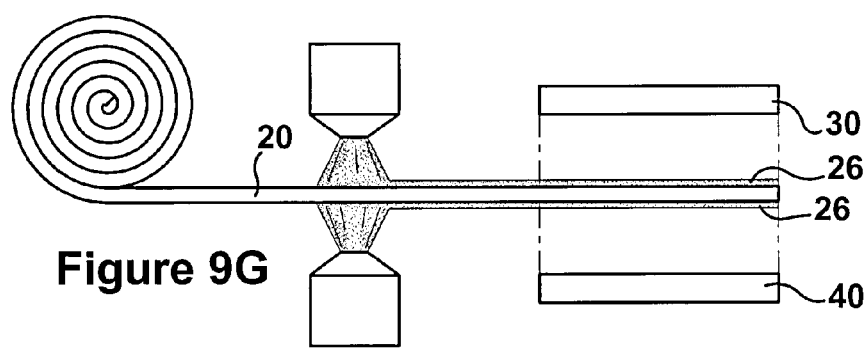

In non-extrusion lamination techniques, an adhesive sublayer 26 can be applied to the fabric 30/40 prior to lamination (FIG. 9G) whereby an adhesive sublayer 26 will be positioned between the elastic layer 20 and one/both of the fabric layers 30/40. The adhesive can comprise hot-melt adhesives (e.g., hot-melt rubber-based materials or acrylic-based materials) and/or non-hot-melt adhesives, such as pressure sensitive adhesives, polyurethane adhesives and structural adhesives. The adhesive sublayer(s) 26 can extend across the entire bonding area, and/or can be applied in intermittent adhesive patterns (e.g., stripes, spots, swirls, islands, grids, checkerboard, voids, random, semi-random, etc.). However, In many instances, it may be best to provide at least to-be-severed areas with substantially complete adhesive bonding.

Figure 9H:
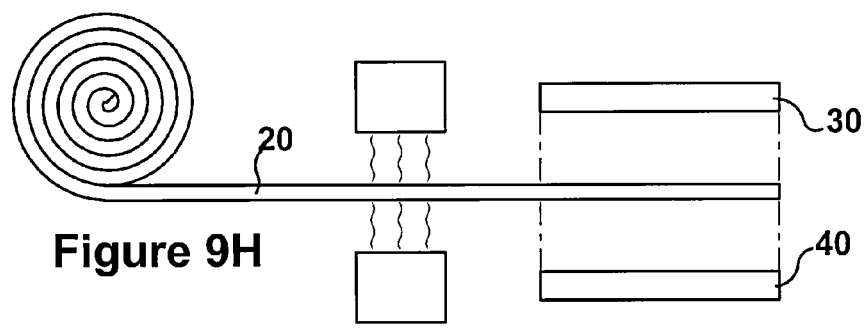
Figure 9I:
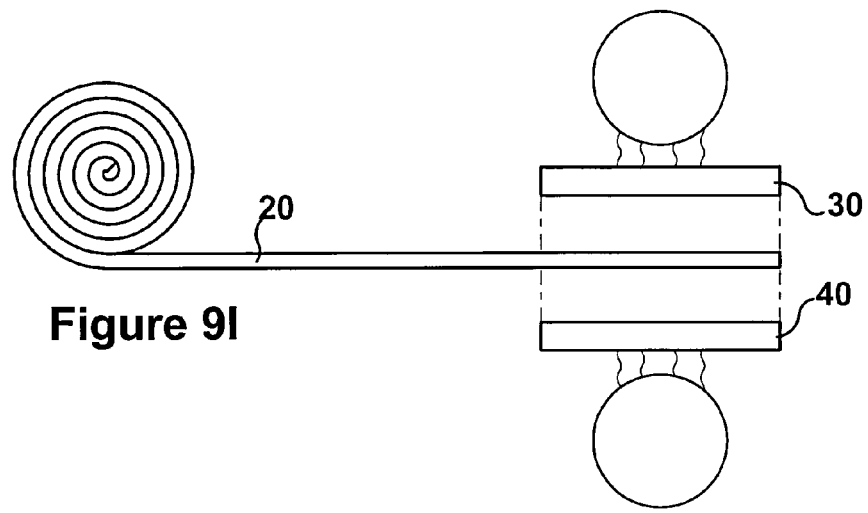
Figure 9J:
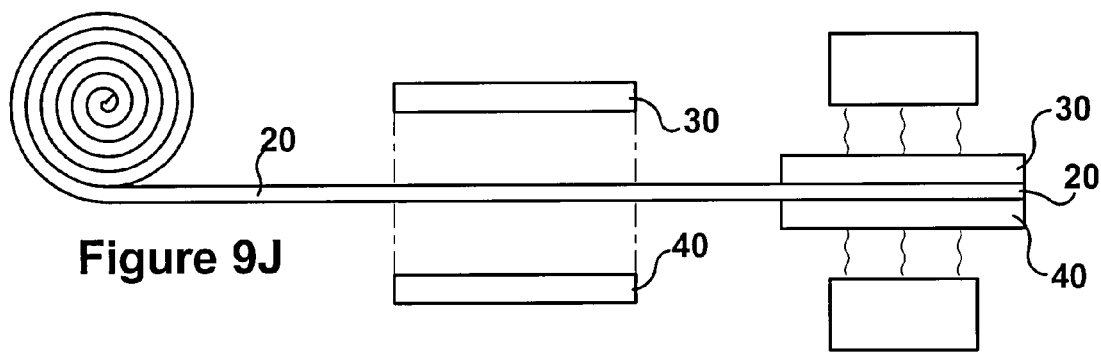
Figure 9K:
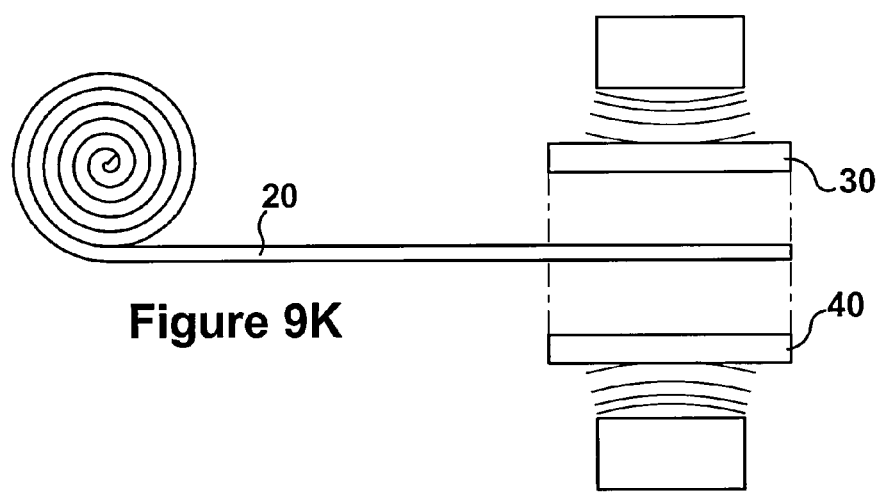
Figure 9L:
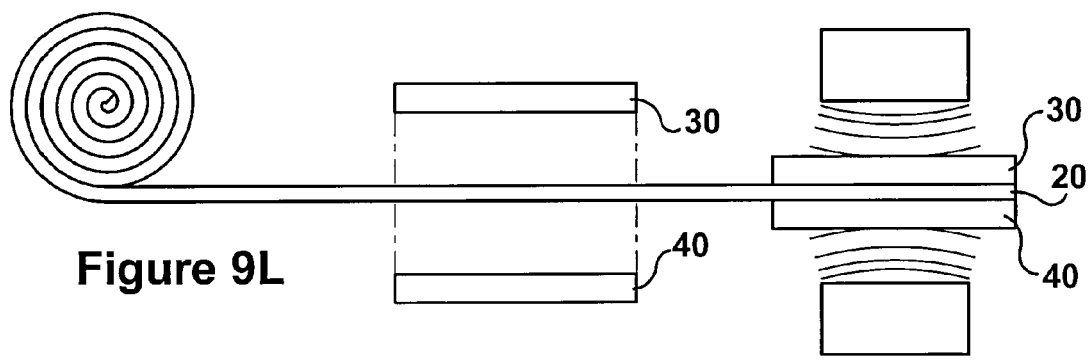
Figure 10C:
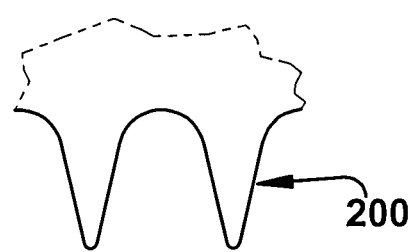
Figure 10D:
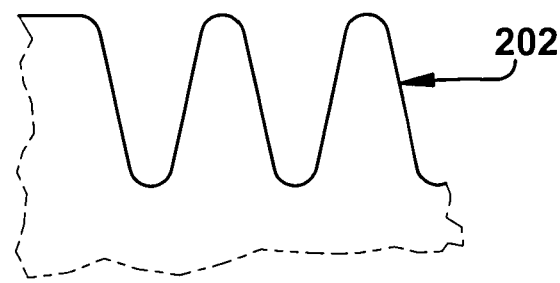

Instead of adhesive bonding, radiant heat can be used to melt the fabric layers 30/40 and/or the elastic layer 20 into a molten state which will then bond the layers together upon cooling (FIGS. 9H-9J). For example, heat can be applied upstream of layer-compiling (FIG. 9H), during layer-compiling (FIG. 9I), or downstream of layer-compiling (FIG. 9J). With particular reference to a heat-applying step during layer-compiling (FIG. 9H), the heat can be supplied, for example, through the laminating rollers. Ultrasonic bonding and/or welding can also be used when laminating the fabric layer(s) 30/40 to the elastic layer 20 (FIGS. 9K and 9L).

The separation of the fabric layers 30/40 into the fabric segments 31/41 is accomplished by rupturing the non-severed regions of the interruptions 32/42. The rupturing steps are performed by applying a series of discrete rupture-inducing forces on the laminate 10. If the severed interruption regions are uniform, and the discrete rupturing forces are uniformly applied, this should result in the elastic qualities being substantially the same across the laminate 10. The application of discrete rupturing forces provides a predictability and/or uniformity that is usually far superior to that achieved by full-width stretching and/or zone-stretching.

The discrete rupture-inducing forces can be applied by pressing a series of rupturing elements against the fabric layers 30/40 along the cross-direction (C), such as the rupturing elements 200/202 shown in FIGS. 10A-10D. The rupturing elements 200/202 each comprise a profile (e.g., corrugated, concave/convex, toothed, etc.) which varies in the thickness dimension along the cross-direction C and which is complementary (e.g., it intermeshes, engages, mates, etc.) with the profile of the other rupturing element 202/200. The rupturing elements 200/202 can be carried on press-like members which are raised/lowered for contact. Alternatively, as shown, the rupturing elements 200/202 can be carried by rollers 204/206 which rotate in the machine direction (M) to draw the material therethrough.

In the illustrated embodiment, the rupturing elements 200/202 are integral parts of rollers 204/206. However, the rupturing elements 200/202 could instead comprise separate disk-shaped elements compiled on a shaft to create the rollers 204/206. In this case, the rupturing profile could be the result of diameter differences between adjacent and/or engaging rupture elements 200/202. When separate elements 200/202 are used, less intermeshing may be required, which may be desirable in some circumstances to, for example, reduce the risk of damage to the elastic layer 20.

The rupturing elements 200/202 and/or the rupturing rollers 204/206 may resemble analogous elements/rollers often used to incrementally stretch nonelastic nonwoven fabrics. However, the rupturing steps employed in the present method are quite different from incremental stretching steps as fiber rupturing is the desired result. Elongation, stretching, re-orientating fabric fibers is not necessary and in most cases will not occur to a substantial degree. The difference between the present rupturing steps and incremental stretching is also evident from casual observation of the finished product. An incrementally stretched nonwoven will take on a wavy, creased, or wrinkled geometry in a relaxed condition. In contrast, fabric segments 31/41 formed by incremental rupturing remain relatively planar (e.g., flat) thereby providing a smoother, neater appearance.

The incremental rupturing steps can be performed simultaneously, or sequentially, on the fabric layers 30/40. Also, the incremental rupturing steps can be performed in stages with the rupturing elements 200/202 having the same, or a successively deeper, three-dimensional profile. The incremental rupturing steps are uniform and/or evenly spaced in the cross direction (C) and/or the machine direction (M), or they may be varied to form patches of different elasticity and/or to accommodate different severing patterns.

Figure 11A:
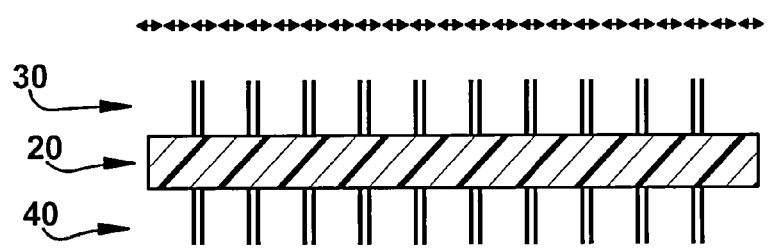
FIGS. 11A-11D are some schematic views of possible severing-rupturing combinations.
Figure 11B:
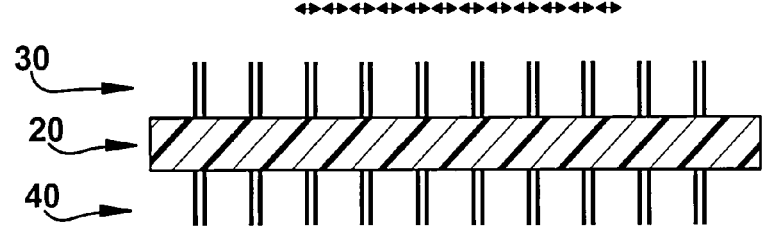

As is best seen by referring to FIGS. 11A-11D, various combinations of rupturing and severing conditions can be used, depending upon the desired laminate outcome. The rupturing can be coextensive with the severed interruption regions and with the elastic layer 20. (FIG. 11A.) Alternatively, the severed interruption regions can be coextensive with elastic layer 20 but the discrete rupturing forces are only applied to portion of the severed laminate 10. (FIG. 11B.) In the latter case, the severed-and-ruptured areas will be highly elastic, with the severed-only areas having perhaps some, but probably less elasticity. This or a similar rupturing-severing relationship may be beneficial when the laminate is used in a product designed to optionally become more elastic, if necessary, during use.

Figure 11C:
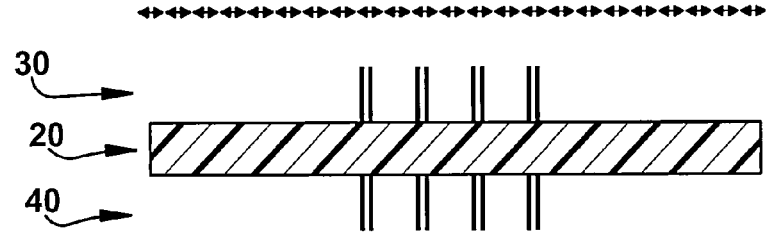

Another option is for the incremental rupturing to be coextensive with elastic layer 20, but not the severing. (FIG. 11C.) The severed-and-ruptured areas will be highly elastic, while the other areas will not. The discrete rupturing forces applied to non-severed areas may result in some rupturing and/or some fabric-segmenting, however complete rupturing without designed weaknesses is usually unlikely. Instead of being ruptured, the non-severed areas may be incrementally stretched, and thereby imparted at least some degree of elasticity. Thus, this or a similar rupturing-severing relationship may be useful when zones of different elasticity are required.

Figure 11D:
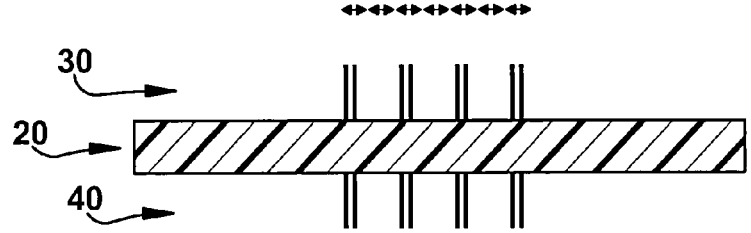

It is further possible for the discrete rupturing forces to be coextensive with the severing, with neither being coextensive with the elastic layer 20. (FIG. 11D.) The severed and ruptured area of the laminate 10 will be highly elastic, while the other areas will not. While these rupturing-severing conditions do not take full advantage of the elastic layer 20, such an arrangement may nonetheless be necessary in certain situations.

Referring now to FIGS. 12A-12F, a side panel 50 including the elastic laminate 10 is shown. The side panel 50 comprises a proximal edge 52, a distal edge 54, an upper edge 56, and a lower edge 58. In an absorbent disposable article 60 (comprising a chassis 62 having a front portion 64, a rear portion 66, a crotch portion 68), the proximal edge of 52 of a side panel 50 is joined to each lateral edge of the chassis rear portion 66 (FIGS. 12G and 12H). The chassis 62 can (or cannot) also incorporate the stretchable laminate 10 (e.g., chassis 112 introduced below).

Figure 12A:
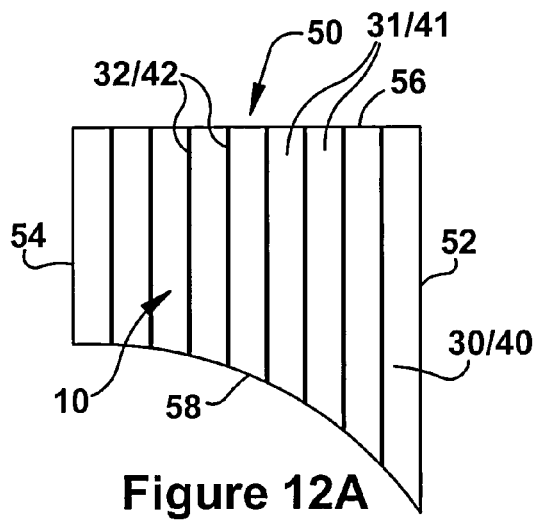
FIGS. 12A-12F are plan views of side panels including a stretchable laminate.
Figure 12D:
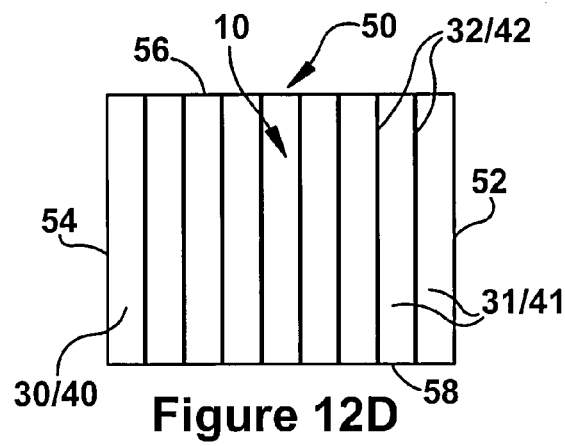
Figure 12B:
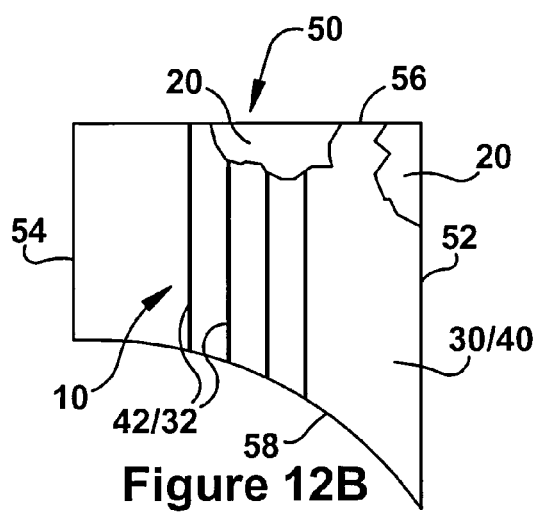
Figure 12E:
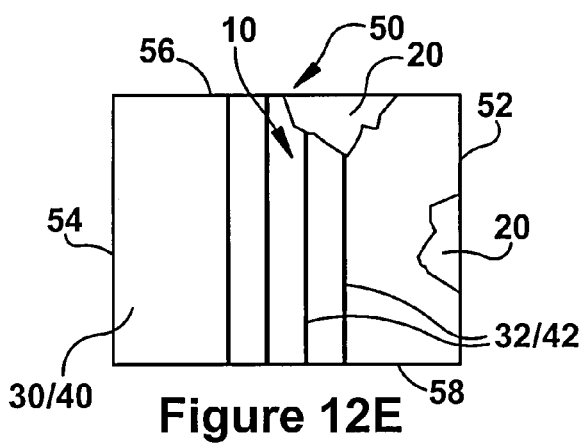
Figure 12C:
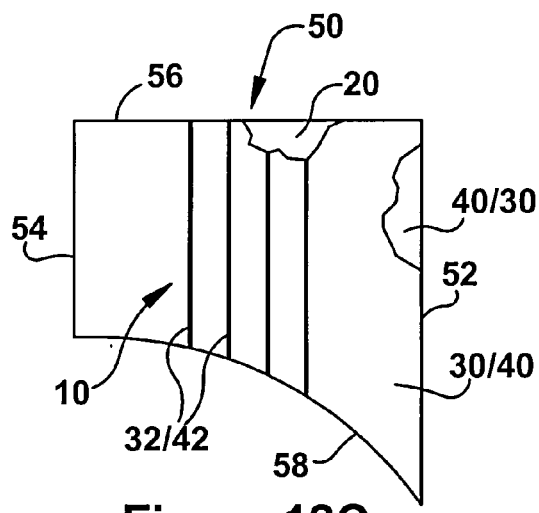
Figure 12F:
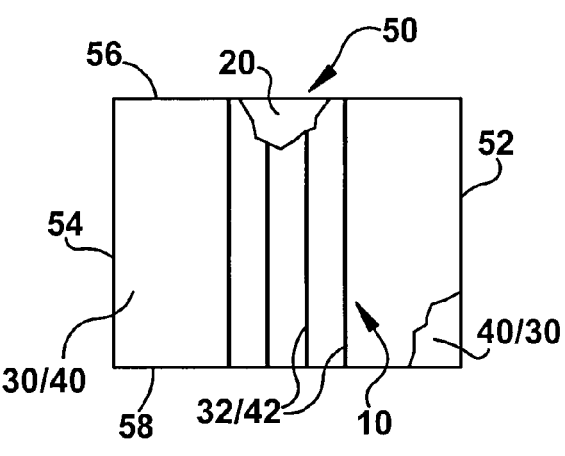
Figure 12G:
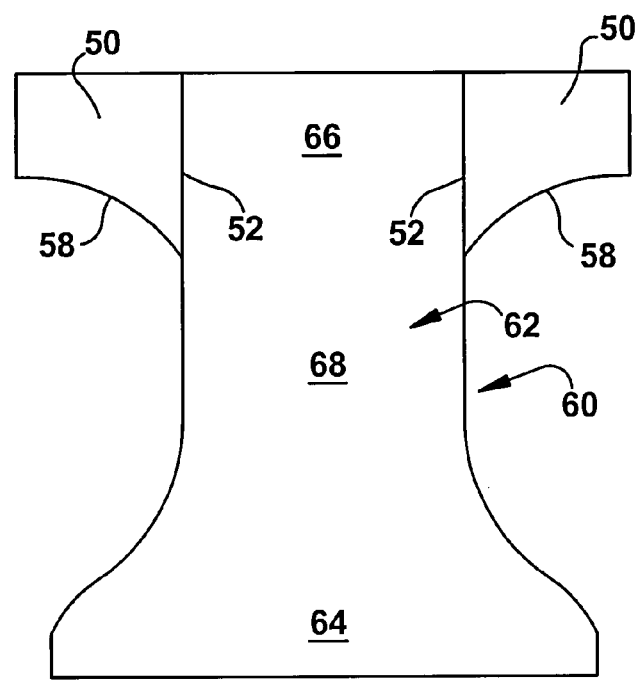
FIGS. 12G and 12H are plan views of absorbent disposable articles each of which includes a pair of side panels.
Figure 12H:
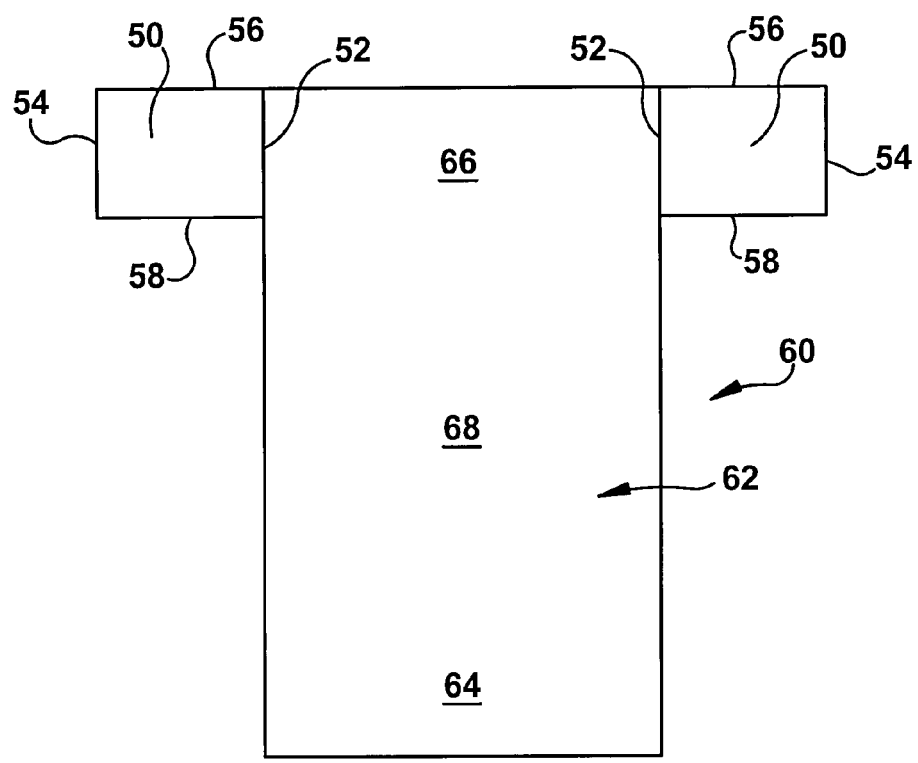

With a baby diaper (FIG. 12G), the lower edge 58 of the side panel 50 can be convexly curved (FIGS. 12A-12C). With an adult incontinence brief (FIG. 12H), the upper edge 56 and the lower edge 58 can be parallel and substantially perpendicular to the proximal edge 52 and/or the distal edge 54 (FIGS. 12D-12F). The first fabric layer 30 can be the next-to-the-skin layer and/or the second fabric layer 40 can be the exposed layer. Alternatively, the first fabric layer 30 can be the exposed layer and/or the second fabric layer 40 can be the next-to-the-skin layer.

With the side panel 50, the cross direction C corresponds to the proximal-distal direction. The machine direction M corresponds to the upper-lower direction. Thus, the side panel 50 is stretchable in the proximal-distal direction and the interruptions 32/42 extend in the upper-lower direction.

The side panel 50 can carry a fastener for attaching its distal edge 54 to the front chassis portion 64 during the diapering process. The fastener can comprise a fastening tape (with attachment means) attached to the side panel 50 and projecting beyond its distal edge 54. Additionally or alternatively, attachment means can be situated on the side panel 50 itself, adjacent the distal edge 54. The attachment means can comprise, for example, mechanical fastening elements (e.g., hooks/loops), adhesive/cohesive area (s), magnetic connections, etc. If the side panel 50 carries a fastening tape, this fastening tape can (or cannot) also incorporate the stretchable laminate 10 (e.g., the fastening tape 70 introduced below).

Figure 13A:
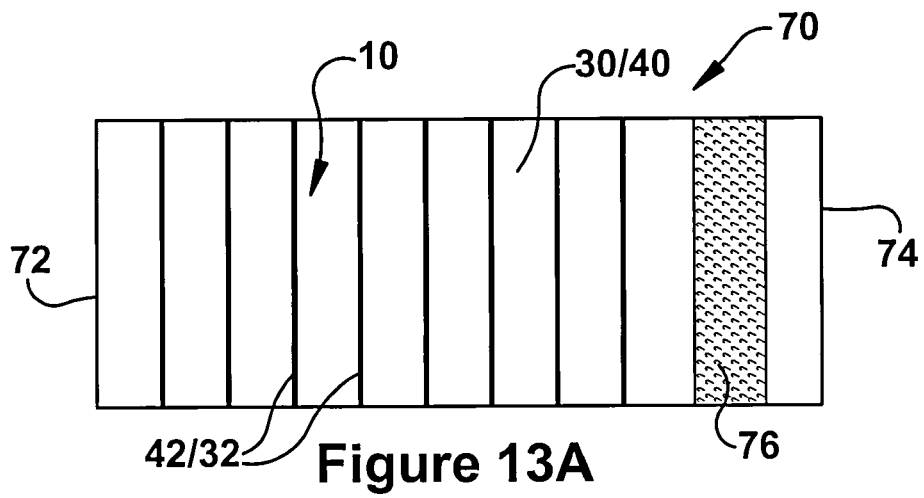
FIGS. 13A-13C are plan views of fastening tapes including a stretchable laminate.
Figure 13B:
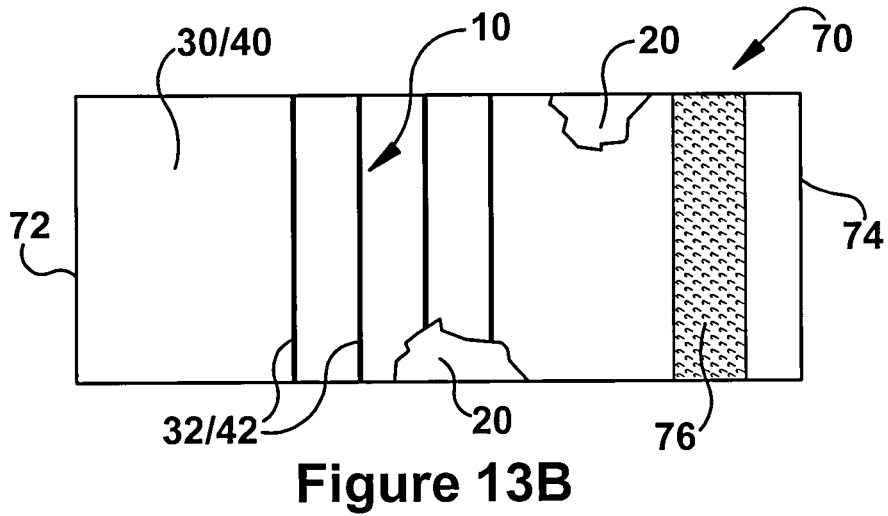
Figure 13C:
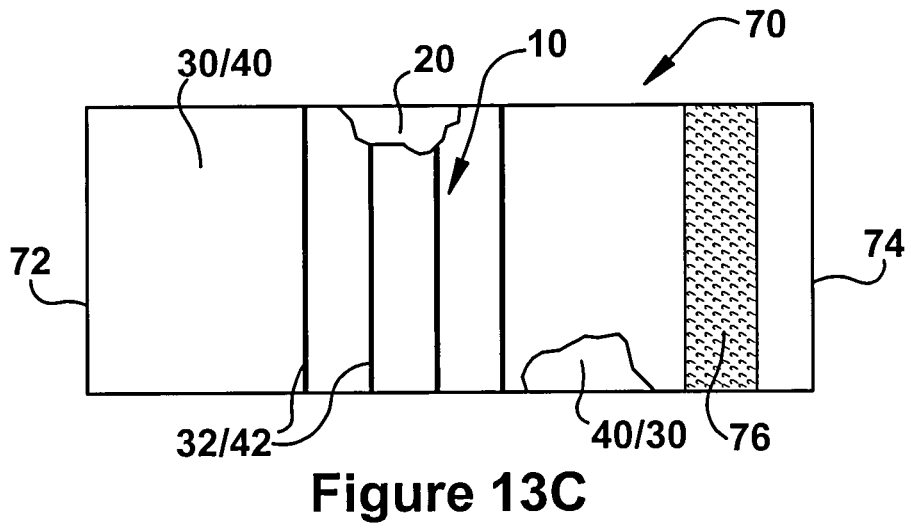
Figure 13D:
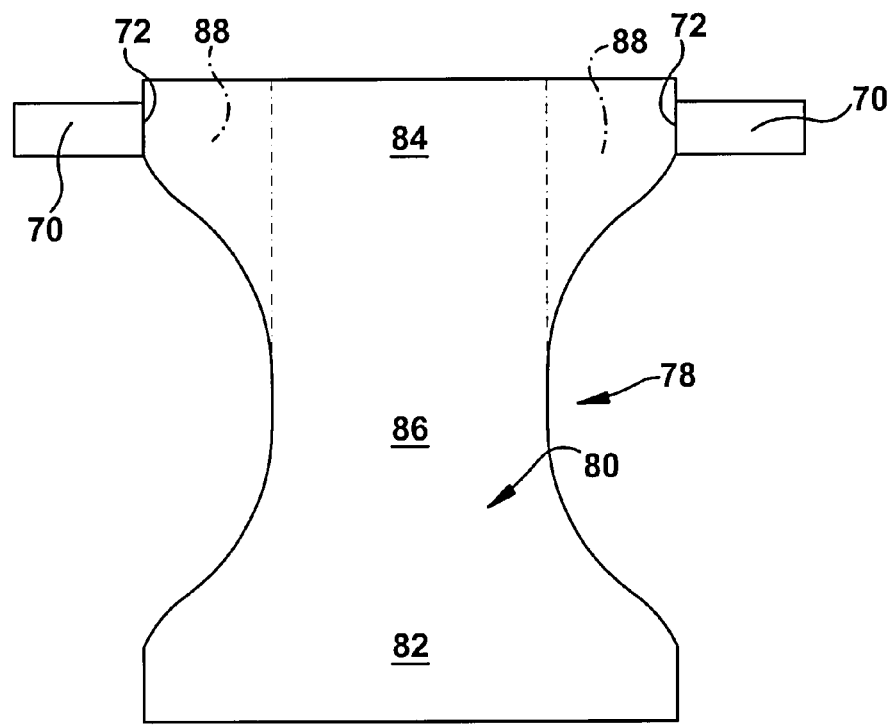
FIGS. 13D and 13E are plan views of absorbent disposable articles each of which includes a pair of such fastening tapes.
Figure 13E:
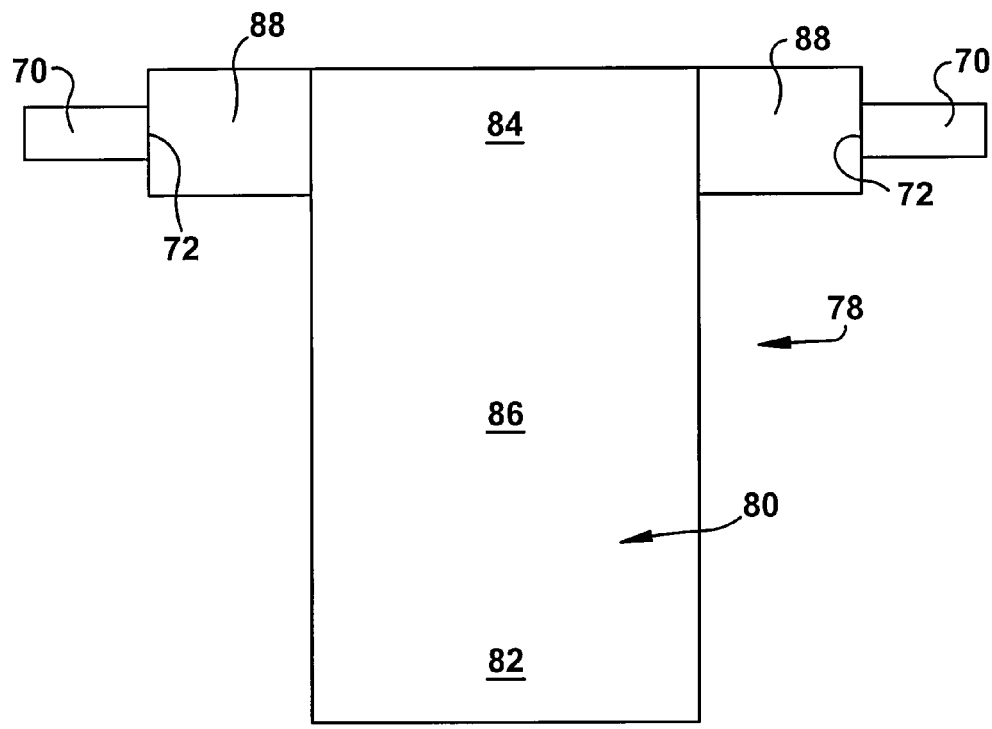

Referring now to FIGS. 13A-13C, a fastening tape 70, having a manufacturer end 72 and a user end 74, includes an elastic laminate 10. The fastening tape 70 can comprise attachment means 76 (e.g., mechanical elements such as hook/loops, adhesive/cohesive area(s), magnetic connections etc.) adjacent its user end 74. When used on an absorbent disposable article 78 (comprising a chassis 80, having a front portion 82, a rear portion 84, and a crotch portion 86, and possible side panels 88), the manufacturer end 72 is joined to the rear chassis portion 84 or the side panel 88 (FIGS. 13D-13E.) The user end 74 is for selective attachment to the front portion 82 of the disposable absorbent article 78 via the attachment means 76. The chassis 80 and/or the side panel 88 can (or cannot) also incorporate the stretchable laminate 10 (e.g., the chassis 112 introduced below and/or the side panel 50 discussed above). The cross direction C in the tape 70 can correspond to its length (i.e., direction between the manufacturer end 72 and the user end 74) and the machine direction M can correspond to its width.

Referring now to FIGS. 14A-14G, a pair of belts 90 can include an elastic laminate 10. The belt's cross direction C can correspond to its length (i.e., direction between the manufacturer end 92 and the user end 94) and the machine direction M can correspond to its width. The laminate 10 can span the entire belt length (FIGS. 14A and 14B) and/or the elastic layer 20 can span the entire belt length (FIGS. 14A-14D). The laminate 10 can span only a portion of the belt length (FIGS. 14C-14F), and can be situated centrally, towards the manufacturer's end 92 (as shown) or towards the user's end 94.

Figure 14G:
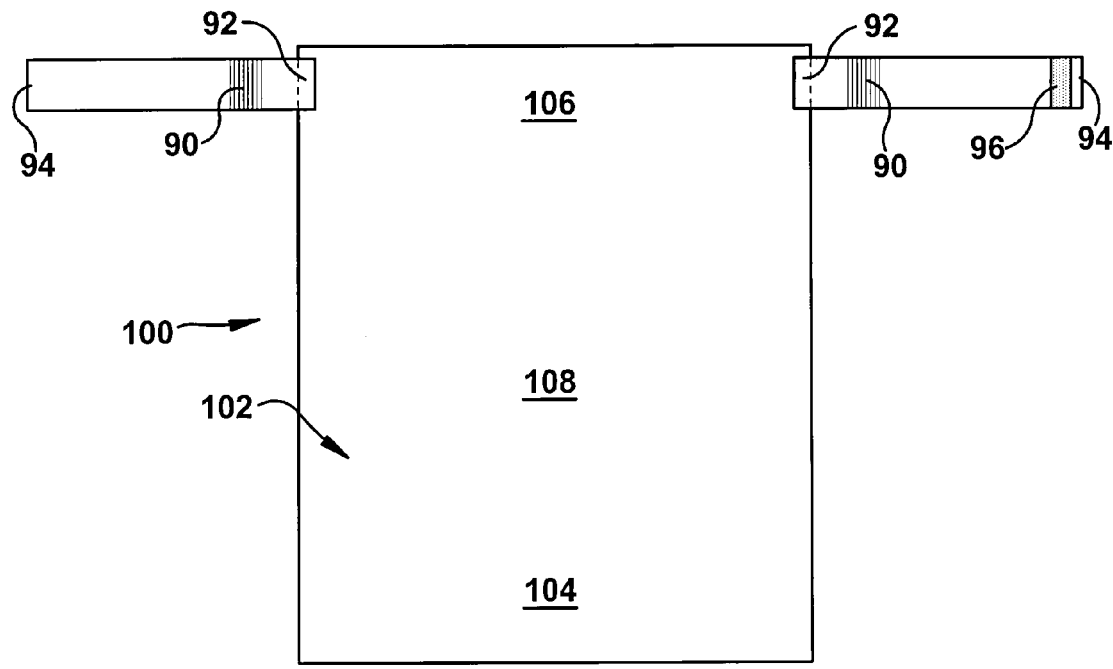
FIG. 14G is a plan view of an absorbent disposable article including a pair of such belts.

At least one belt 90 (FIGS. 14B, 14D, and 14F) can comprise attachment means 96 (e.g., mechanical elements such as hook/loops, adhesive/cohesive area(s), magnetic connections etc.) adjacent its user end 94. When used on an absorbent disposable article 98 (comprising a chassis 100, having a front portion 102, a rear portion 104, and a crotch portion 106), the manufacturer end 92 of each belt 90 is joined to the rear chassis portion 104. (FIG. 14G.) One belt 90 (FIGS. 14A, 14C, and 14E) can be folded around the user's waist and the other belt 90 (FIGS. 14B, 14D, and 14F) can be folded thereover. The belts 90 are held in position by the attachment means 96. The chassis 100 can (or cannot) also incorporate the stretchable laminate 10 (e.g., the chassis 112 introduced below).

Figure 15:
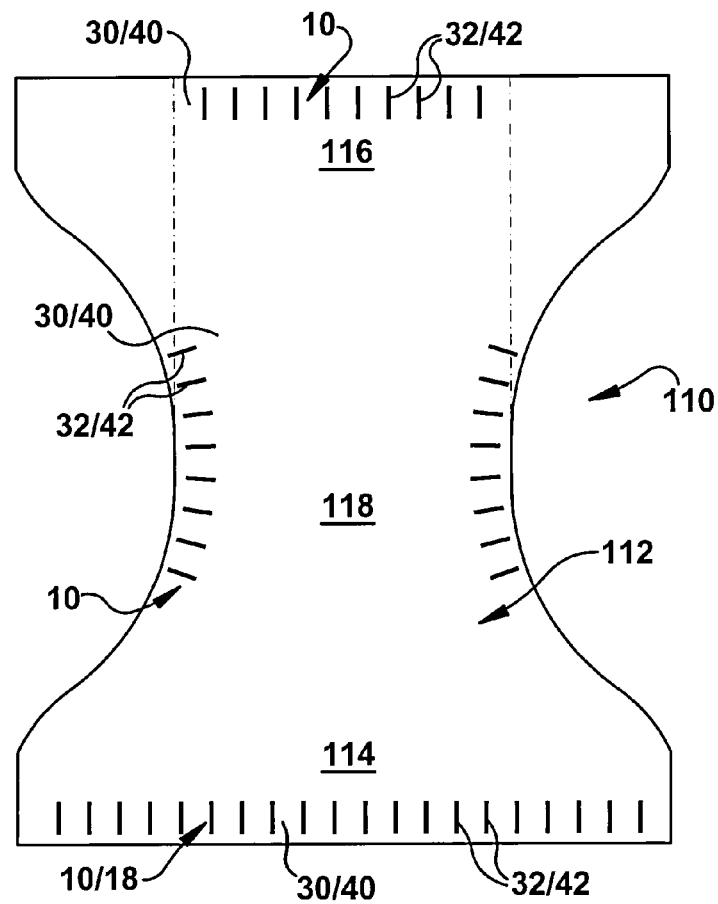
FIG. 15 is a plan view of an absorbent disposable article including a stretchable laminate.

Referring now to FIG. 15, a disposable absorbent article 110 is shown, the article 110 comprising a chassis 112 (having a front portion 114, a rear portion 116, and a crotch portion 118) including an elastic laminate 10. The elastic laminate 10 can form at least part of the front portion 114 of the chassis 112 (e.g., a waist region), at least part of the rear portion 116 of the chassis 112 (e.g., a waist region), and/or at least part of the crotch portion 118 of the chassis 112 (e.g., leg-opening regions). The article 110 can (or cannot) include a side panel incorporating the stretchable laminate 10 (e.g., the side panel 50 introduced above), a fastening tape incorporating the elastic laminate 10 (e.g., the fastening tape 70 introduced above), and/or belts incorporating the elastic laminate 10 (e.g., the belts 90 introduced above).

One may now appreciate the elastic laminate 10 is an excellent candidate for incorporation into a diaper product and/or many other products where elasticity is required. The elasticizing technique hinges on rupturing—not stretching—a fabric layer whereby a wider range of nonwoven fabrics are welcome. Moreover, the ability to alter the severing-rupturing relationship allows the production of customized products with essentially the same severing equipment and/or rupturing equipment.

The invention claimed is:

1. A method of making an elastic laminate, comprising the steps of:
   providing an intermediate laminate comprising an elastic layer and a first fabric layer laminated thereto, the elastic layer being elongatable and recoverable in a cross direction, and
   segmenting the first fabric layer into first fabric segments which diverge in the cross direction upon laminate elongation and converge in the cross direction upon laminate recovery, the first fabric segments being separated by first fabric layer interruptions which extend at least partially through the first fabric layer thickness, each first fabric layer interruption having a proximal region and a distal region;
   wherein said segmenting of the first fabric layer comprises:
   applying a series of discrete rupture-inducing forces in the cross-direction to rupture the first fabric layer to form a proximal or distal region; and
   applying a series of sharply-severing cuts to form a proximal or distal region.

2. The method as set forth in claim 1, wherein the intermediate laminate further comprises a second fabric layer and wherein the elastic layer is sandwiched between the first fabric layer and the second fabric layer, and said method further comprises the step of:
   segmenting the second fabric layer into second fabric segments which diverge in the cross direction upon elongation of the elastic layer and converge in the cross direction upon recovery of the elastic layer, the second fabric segments being separated by second fabric layer interruptions which extend at least partially through the second fabric layer thickness, each second fabric layer interruption having a proximal region and a distal region;
   wherein said segmenting of the second fabric layer comprises applying a series of discrete rupture-inducing forces in the cross-direction to rupture the second fabric layer, thereby forming at least one of the proximal or the distal regions of the second fabric layer interruptions.

3. The method as set forth in claim 2, wherein said segmenting of the first fabric layer and said segmenting of the second fabric layer are performed substantially simultaneously.

4. The method as set forth in claim 1, wherein the discrete rupture-inducing forces are applied in increments corresponding to the spacing of the first fabric segments.

5. The method as set forth in claim 4, wherein the discrete rupture-inducing forces are applied by pressing a series of rupturing elements against the first fabric layer along the cross-direction.

6. The method as set forth in claim 5, wherein each rupturing element has a profile which varies in the thickness dimension along the cross-direction.

7. The method as set forth in claim 1, wherein the discrete rupture-inducing forces are applied by passing the first fabric layer between mated sets of rupturing elements, said mated sets of rupturing elements including a first set of rupturing elements and a second set of rupturing elements, said second set of rupturing elements being complementary to the first set of rupturing elements.

8. The method as set forth in claim 1, wherein the rupturing is performed by at least one roller which rotates in the machine direction.

9. The method as set forth in claim 1, wherein said step of providing the intermediate laminate comprises forming at least a portion of the first fabric layer interruptions in the first fabric layer prior to said segmenting of the first fabric layer.

10. The method as set forth in claim 9, wherein said forming comprises at least one of die-cutting, kiss-cutting, slitting, scoring, laser-cutting or ultrasound-cutting of the first fabric layer.

11. The method as set forth in claim 9, wherein said forming is performed prior to laminating said first fabric layer to the elastic layer.

12. The method as set forth in claim 11, wherein said laminating is performed in-line with said rupturing.

13. The method as set forth in claim 1, wherein said laminating the first fabric layer to the elastic layer comprise at least one of adhesive, extrusion, heat or ultrasonic bonding of the first fabric layer to the elastic layer.

14. The method as set forth in claim 1, wherein the first fabric layer interruptions extend in a path non-parallel to the cross direction.

15. The method as set forth in claim 14, wherein the first fabric layer interruptions extend in a path substantially parallel to the machine direction.

16. An absorbent article including an elastic laminate made in accordance with a method comprising the steps of:
   providing an intermediate laminate comprising an elastic layer and a first fabric layer laminated thereto, the elastic layer being elongatable and recoverable in a cross direction, and
   segmenting the first fabric layer into first fabric segments which diverge in the cross direction upon laminate elongation and converge in the cross direction upon laminate recovery, the first fabric segments being separated by first fabric layer interruptions which extend at least partially through the first fabric layer thickness, each first fabric layer interruption having a proximal region and a distal region;
   wherein said segmenting of the first fabric layer comprises:
   applying a series of discrete rupture-inducing forces in the cross-direction to rupture the first fabric layer to form a proximal or distal region; and
   applying a series of sharply-severing cuts to form a proximal or distal region.

17. An elastic laminate comprising:
   an elastic layer that is elongatable and recoverable in a first direction; and,
   a first fabric layer laminated to the elastic layer, said first fabric layer being segmented into first fabric segments which diverge from one another in the first direction upon elongation of the elastic layer and which converge toward one another in the first direction upon recovery of the elastic layer, the first fabric segments being separated from one another by first fabric layer interruptions which extend at least partially through a thickness of the first fabric layer, each first fabric layer interruption having a proximal region adjacent the elastic layer and a distal region spaced apart from the elastic region by at least the proximal region of the corresponding first fabric layer interruption;
   wherein at least one of the proximal or the distal regions of the first fabric layer interruptions are created by applying a series of discrete rupture-inducing forces to the first fabric layer in the first direction to rupture the first fabric layer; and
   wherein at least one of the proximal or the distal regions of the first fabric layer interruptions are sharply severed.

18. The elastic laminate of claim 17, further comprising:
   a second fabric layer laminated to the elastic layer, said second fabric layer being segmented into second fabric segments which diverge from one another in the first direction upon elongation of the elastic layer and which converge toward one another in the first direction upon recovery of the elastic layer, the second fabric segments being separated from one another by second fabric layer interruptions which extend at least partially through a thickness of the second fabric layer, each second fabric layer interruption having a proximal region adjacent the elastic layer and a distal region spaced apart from the elastic region by at least the proximal region of the corresponding second fabric layer interruption;
   wherein at least one of the proximal or the distal regions of the second fabric layer interruptions are created by applying a series of discrete rupture-inducing forces to the second fabric layer in the first direction to rupture the second fabric layer.

19. The elastic laminate of claim 17, wherein the regions of the first fabric layer that are sharply severed are formed by at least one of die-cutting, kiss-cutting, slitting, scoring, laser-cutting or ultrasound-cutting of the first fabric layer.

20. The elastic laminate of claim 18, wherein at least one of the proximal or the distal regions of the second fabric layer interruptions are further created by at least one of die-cutting, kiss-cutting, slitting, scoring, laser-cutting or ultrasound-cutting of the second fabric layer.

21. The elastic laminate of claim 17, wherein the elastic layer is not non-coextensive with the first fabric layer.

* * * * *